United States Patent [19]

Tobler et al.

[11] 4,394,156

[45] Jul. 19, 1983

[54] NOVEL N-PHENYL-SUBSTITUTED N-HETEROCYCLIC COMPOUNDS, THEIR PREPARATION AND USE IN AGENTS FOR REGULATING PLANT GROWTH

[75] Inventors: Hans Tobler, Allschwil; Werner Föry, Basel; Rolf Schurter, Binningen, all of Switzerland

[73] Assignee: Ciba-Geigy Corporation, Ardsley, N.Y.

[21] Appl. No.: 314,620

[22] Filed: Oct. 26, 1981

Related U.S. Application Data

[60] Continuation-in-part of Ser. No. 111,517, Jan. 14, 1980, abandoned, which is a division of Ser. No. 896,970, Apr. 12, 1978, Pat. No. 4,208,202.

[30] Foreign Application Priority Data

Apr. 15, 1977 [CH] Switzerland ............ 4702/77
Nov. 9, 1977 [CH] Switzerland ............ 13661/77

[51] Int. Cl.³ .............. A01N 43/40; C01D 213/62; C07D 213/64; C07D 213/68
[52] U.S. Cl. .............................. 71/94; 546/12; 546/288; 546/290; 546/296; 546/215; 546/216; 548/543; 548/544; 260/239.3 R; 71/88; 71/95

[58] Field of Search ............. 546/215, 221, 12, 288, 546/290, 296; 260/326.5 FL, 326.5 S, 326.82; 71/94, 95

[56] References Cited

U.S. PATENT DOCUMENTS 4,208,202 6/1980 Tobler et al. ............ 546/215

*Primary Examiner*—Robert T. Bond
*Attorney, Agent, or Firm*—Frederick H. Rabin

[57] ABSTRACT

The present invention relates to novel active compounds having a plant growth-inhibiting and herbicidal action and their preparation and to agents containing these active ingredients, and their use.

The novel active compounds are saturated and unsaturated 4-membered to 7-membered ring nitrogen heterocyclic compounds which are substituted on the nitrogen atom by a phenyl radical which itself carries a trifluoromethanesulphonamido group -NH-SO$_2$-CF$_3$ as a substituent. The phenyl radical can also carry other substituents and the heterocyclic structure can also be substituted. Oxo derivatives of the heterocyclic compound, in which the oxo group is preferably adjacent to the nitrogen atom, form a preferred sub-group of compounds.

8 Claims, No Drawings

NOVEL N-PHENYL-SUBSTITUTED N-HETEROCYCLIC COMPOUNDS, THEIR PREPARATION AND USE IN AGENTS FOR REGULATING PLANT GROWTH

CROSS REFERENCE TO RELATED APPLICATIONS

This is a continuation-in-part of application Ser. No. 111,517 filed on Jan. 14, 1980, now abandoned which is a divisional of application 896970 filed on Apr. 12, 1978, now U.S. Pat. No. 4,208,202.

The present invention relates to novel N-phenyl-substituted 4-membered to 7-membered ring N-heterocyclic compounds and processes for their preparation and also to agents for regulating plant growth, especially herbicidal and plant growth-inhibiting agents, which contain these novel active compounds as the active component, and also processes for regulating plant growth, especially for the pre-emergence and post-emergence combating of weeds and for inhibiting plant growth, using the novel active compounds and the agents containing them.

The novel N-heterocyclic compounds of the present application are of the formula I

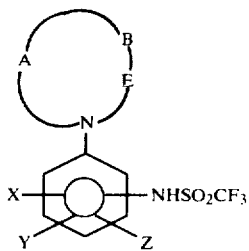

In this formula either: A+B+E together are a $C_3$-$C_6$ alkylene, $C_3$-$C_6$ alkenylene or $C_4$-$C_5$ alkadienylene chain, which can be substituted by one or more radicals from the group comprising halogen, cyano, alkyl, lower alkoxy, alkoxyalkoxy, alkylcarbonyloxy, alkenylcarbonyloxy and alkylthio and benzoyloxy, benzylthio or phenylthio radicals, which can be substituted in the nucleus, or A+B+E together are a $C_3$-$C_4$ alkenylene or alkadienylene chain which additionally also contains a carbonyl group

at the start of or within the chain and can be substituted by carboxyl, alkoxycarbonyl or one or more radicals from the group of substituents listed above, or: A is a carbonyl radical

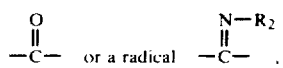

B is a $C_1$-$C_4$ alkylene, $C_2$-$C_4$ alkenylene or $C_4$-alkadienylene chain, which can be substituted by one or more radicals from the abovementioned groups, and E is a bridge member

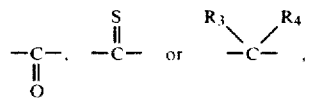

where $R_2$ is hydrogen, $C_3$-$C_5$ alkenyl or $C_1$-$C_8$ alkyl, which latter radical can be substituted by one or more alkoxy, alkoxyalkoxy, alk(en)ylcarbonyloxy, benzoyl or phenyl radicals, which, in turn, can carry substituents from the group comprising halogen, alkyl, nitro, $CF_3$, cyano or alkoxy, and $R_3$ and $R_4$ are each hydrogen or $C_1$-$C_4$ alkyl, and X, Y and Z independently of one another are each hydrogen, halogen, $C_1$-$C_4$ alkyl or halogenoalkyl, cyano, nitro, —CS—$NH_2$, substituted or unsubstituted benzyl or a group —S(O)$_n$—$R_6$, —OR$_7$, —COOR$_8$, —SO$_2$—N($R_{10}$)$_2$ or —N($R_{11}$)$_2$, in which n is a number from nought to 2, $R_6$ is $C_1$-$C_5$ alkyl, or phenyl or phenylalkyl, which can be substituted in the nucleus, $R_7$ is $C_1$-$C_5$ alkyl, alkoxyalkyl, alkoxyalkoxyalkyl, alk(en)ylcarbonyl, or phenyl or benzoyl which can be substituted by lower alkyl, halogen, CN, $CF_3$ or $NO_2$, $R_8$ is hydrogen or lower alkyl, $R_{10}$ is lower ($C_1$-$C_4$) alkyl and $R_{11}$ is hydrogen or $C_1$-$C_4$ alkyl.

If A is a —CO group, B is a $C_1$-$C_4$ alkylene chain and E is a bridge member of the type

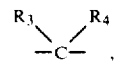

the compounds are 4-membered to 7-membered ring lactams which are substituted on the nitrogen atom (1-position) by a trifluoromethanesulphonamido group, i.e. azetidin-2-one, pyrrolidin-2-ones, piperidin-2-ones and hexahydroazepin-2-ones. Preferred compounds are the 5-membered and 6-membered ring heterocyclic compounds, i.e. the pyrrolidin-2-ones and piperidin-2-ones. In addition to the —NH—$SO_2$—$CF_3$ group, the phenyl ring preferably carries 1 or 2 further radicals, for example methyl.

If the radicals A+B+E together are a saturated or unsaturated $C_3$—$C_6$ chain member, the compounds are cyclic, saturated or unsaturated 4-membered to 7-membered cyclic amines, such as pyrroles, pyridines, piperidines, pyrrolidines and the like.

If the radicals A+B+E together are an unsaturated $C_3$-$C_4$ chain member (alkenylene or alkadienylene), which also additionally contains a carbonyl group at the start of or within the chain, the compounds are substituted or unsubstituted pyrrolinones or pyridones.

If both A and E are the —CO group, the compounds are dicarboxylic acid phenylimides.

Finally, when A is the bridge member

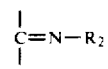

the compounds are cyclic amidines.

If the heterocyclic structure is substituted in a 2-membered to 5-membered saturated alkylene bridge, it can be monosubstituted or disubstituted on one or more —$CH_2$ groups. The preferred halogen substituent is chlorine. Lower alkyl and alkoxy radicals, as substituents, have 1 to 6 C atoms but methyl and methoxy are preferred.

Preferred positions of methyl and methoxy radicals are the 3-position (adjacent to a keto group A) and the other position adjacent to the ring nitrogen atom.

The —NHSO₂CF₃ group is capable of forming salts in which the hydrogen atom has been replaced by a cation X, preferably by sodium or potassium or an organic amine cation. Amongst organic amines, diethanolamine has proved particularly suitable.

Metal cations X can also be those of the alkaline earth metals or of zinc, copper, iron and the like. If the cation present is divalent or trivalent, it is, or course, linked to the number of anions of the parent body I which corresponds to its valency. There is then 1/m cation of valency m per parent body I.

N-Phenyl-substituted pyrrolidin-2-ones, piperidin-2-ones and azetidin-2-ones having a herbicidal action have already been disclosed in U.S. Pat. Nos. 3,238,222 and 3,958,974, but these compounds have different substituents in the phenyl ring.

On the other hand, perfluoroalkanesulphoanilide derivatives having a herbidical action have been described in U.S. Pat. No. 3,920,444 and in German Offenlegungsschrift No. 2,364,144, but these compounds do not contain a heterocyclic grouping.

It has now been found, surprisingly, that the novel heterocyclic active compounds, according to the invention, of the formula I are clearly superior to the active compounds known from the above literature sources, both in respect of the herbicidal action and in respect of their suitability as plant growth inhibitors.

The process for the preparation of the novel active compounds of the formula I comprises treating a heterocyclic amino-aniline derivative of the formula II

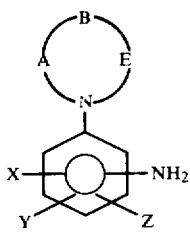

(II)

in which A, B, E, X, Y and Z are as defined under formula I, in a manner known per se with a trifluoromethanesulphonylating agent in the presence of an acid acceptor and, if desired, converting the trifluoromethanesulphonamide thus obtained into the salt of a base or of an amine.

The agent used to introduce the trifluoromethanesulphonic acid group can be the anhydride of trifluoromethanesulphonic acid (CF₃SO₂)₂O or a halide of this acid of the formula CF₃-SO₂-Hal, in which Hal is preferably fluorine or chlorine.

The acid acceptors used are the ammonium bases, alkali metal hydroxides, carbonates and bicarbonates and alkaline earth metal hydroxides, carbonates and bicarbonates, and also primary, secondary and tertiary amines, for example triethylamine or N,N-dimethylaniline, customary for such acylations.

The starting amines of the formula II are also novel substances which have not yet been described in the literature. They are prepared by methods known per se, for example in accordance with the processes which are described in U.S. Pat. Nos. 3,238,222, 3,958,974, 3,576,814 and 4,051,142 for similar N-phenyl-substituted N-heterocyclic compounds.

In principle, the novel intermediates of the formula II are prepared by adding the heterocyclic structure onto a starting aniline of the formula III

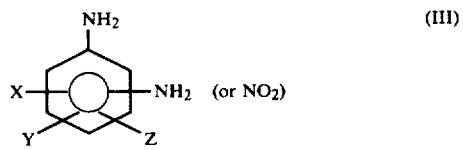

(III)

If the starting material of the formula III which is used is a nitroaniline, which is frequently to be preferred in order to prevent the formation of structural isomers, it is necessary, after adding the heterocyclic structure onto the amino group in the 1-position, to convert the nitro group into an amino group by hydrogenation or reduction, in accordance with well-known methods.

Cyclic 5-membered to 7-membered ring lactams (A=—CO— and

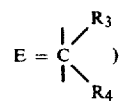

are best prepared by the methods described in German Pat. No. 850,007, in U.S. Pat. No. 3,862,172, in German Reichspatent No. 609,244 and in J. Org. Chem. 14, 862 (1949) and J. Org. Chem. 26, 718 and also by reacting an aniline of the formula III with a lactone

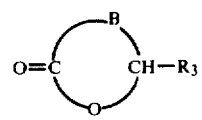

at elevated temperature (100°–250° C.) in accordance with U.S. Pat. No. 3,238,222.

The process according to U.S. Pat. No. 3,958,974 can be employed in order to prepare a 4-membered ring lactam (azetidin-2-one), by converting a nitroaniline of the formula III, by means of β-chloro-propionyl chloride, into the corresponding N-(nitrophenyl)-β-chloropropionamide and allowing this to react at room temperature with a compound CH₃SOCH₂Na or CH₃SO₂CH₂Na, formed from sodium hydride and excess dimethylsulphoxide, and hydrogenating or reducing the nitro group in the corresponding 1-(nitrophenyl)-azetidin-2-one to the amino group.

4-membered to 7-membered cyclic amines (A+B+E are a C₃-C₆ chain member) are best prepared analogously to Houben-Weyl 11, 1, 580 (1957) and pyrroles are best prepared analogously to J. Heterocyclic Chem. 14, 172 (1977).

Imides (A and E are each a —CO group) are prepared analogously to J. Am. Soc. 67, 227 (1945) and cyclic amidines

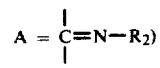

are prepared in accordance with U.S. Pat. No. 2,513,270 [Chem. Abstr. 45, 5,187 (1951)].

If the heterocyclic structure in the intermediates of the formula II is substituted by halogen, this halogen can be replaced by a cyano group or an alkoxy group by reaction with KCN or an alkanolate.

All of the reactions mentioned are preferably carried out in solvents and diluents which are inert towards the reactants.

Preferred solvents are polar organic solvents, such as alcohols, ketones, dimethylformamide, tetrahydrofurane, dimethylsulphoxide and the like.

A preferred sub-group of active compounds of the general formula I comprises those in which A+B+E together correspond to the first-mentioned definition of a chain (without a carbonyl group) and those for which the given individual definition of the radicals A, B and E applies.

Finally, preferred active compounds are those of the more restricted formula

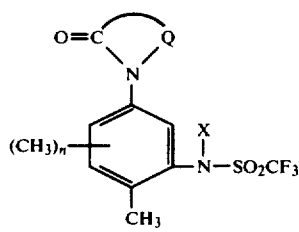

(Ia)

in which Q is an alkylene radical having 2 to 5 C atoms, which is unsubstituted or monosubstituted to polysubstituted by halogen, cyano or lower alkyl or alkoxy, X is hydrogen or the equivalent of a monovalent to trivalent metal cation or of an inorganic or organic amine or quaternary ammonium cation and n is the number 0 or 1.

The heterocyclic compound is thus an azetidin-2-one, pyrrolidin-2-one, piperidin-2-one or hexahydroazepin-2-one.

The examples given below describe the preparation of several active compounds, according to the invention, of the formula I and of their intermediates of the formula II, required for this. Further intermediates and end products prepared in a corresponding manner are listed in the tables which follow. All of the temperature data are in degrees Centigrade.

EXAMPLE 1

(a) 1-(3'-Nitro-4',6'-dimethylphenyl)-azetidin-2-one 5 g of sodium hydride (in the form of a 55% strength dispersion in oil) are stirred in 100 ml of dimethylsulphoxide until no further evolution of gas can be detected. 21.5 g (0.084 mol) of N-(3-nitro-4,6-dimethylphenyl)-β-chloropropionamide, suspended in 500 ml of tetrahydrofurane, are then added in the course of 5–10 minutes. The reaction temperature is kept at 15° for ½ an hour and water is then added dropwise in order to destroy excess sodium hydride. The reaction solution is taken up in methylene chloride and washed with water and saturated NaCl solution, dried (MgSO₄) and evaporated. The crude product is subjected to fractional filtration on silica gel in chloroform. This gives 14.5 g (78%) of product; melting point 102°.

$C_{11}H_{12}N_2O_3$ (220.23); calculated: C 60.00; H, 5.50; N 12.72%; found: C 60.1; H 5.5; N 12.7%.

(b) 1-(3'-Amino-4',6'-dimethylphenyl)azetidin-2-one 21.2 g (0.0965 mol) of the 1-(3'-nitro-4',6'-dimethylphenyl)-azetidin-2-one obtained according to a) are hydrogenated in 210 ml of methanol with 2 g of Raney nickel at 30°–35° under normal pressure. The reaction solution is filtered and evaporated. Recrystallisation of the crude product from methanol gives 16.6 g (90%) of crystals having a melting point of 123°–124°.

$C_{11}H_{14}N_2O$ (190.25) calculated: C 69.45; H 7.42; N 14.73%; found: C 69.5; H 7.3; N 14.9%.

(c) 1-(3'-Trifluoromethanesulphonamido-4',6'-dimethylphenyl)-azetidin-2-one 12 g (0.04 mol) of trifluoromethanesulphonic acid anhydride are added dropwise in the course of 15 minutes, at −40°, to a solution of 6.6 g (0.035 mol) of 1-(3'-amino-4',6'-dimethylphenyl)-azetidin-2-one and 4.3 g (0.041 mol) of triethylamine in 100 ml of chloroform. After warming to room temperature, the clear solution is extracted twice with 200 ml of 1 N KOH. The aqueous extract is filtered, cooled and acidified with concentrated hydrochloric acid. The product thus precipitated is filtered off and washed with water until neutral. It is dried in a desiccator at 50°. The yield is 4.9 g (43%); melting point 137°–139°.

The product has the formula

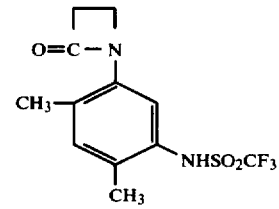

The diethanolamine salt of this compound is a viscous oil.

Analysis: $C_{12}H_{13}F_3N_2O_3S$ (322.30); calculated: C 44.72; H 4.07; F 17.0; N 8.69; S 9.95%; found: C 44.9; H 4.0; F 17.9; N 8.8; S 9.7%.

EXAMPLE 2

(a) 1-(3'-Nitro-4',6'-dimethylphenyl)-piperidin-2-one 77 g (0.27 mol) of N-(3-nitro-4,6-dimethylphenyl)-δ-chlorovaleroylamide are stirred vigorously in a mixture of 50 ml of tetrahydrofurane and 500 ml of 22% strength aqueous sodium hydroxide solution for 5 hours at 60°–65°. The reaction mixture is diluted with water, cooled and acidified with hydrochloric acid. The product which has precipitated is washed until neutral and dried in a desiccator at 70°. This gives 62.8 g (93%); melting point 134°–135°.

$C_{13}H_{16}N_2O_3$ (248.28); calculated: C 62.89; H 6.50; N 11.28%; found: C 63.1; H 6.5; N 11.7%.

(b)

The hydrogenation to 1-(3'-amino-4',6'-dimethylphenyl)piperidin-2-one with a melting point of 133°–135° is carried out in the same way as described in Example 1b for the corresponding 4-membered ring heterocyclic compound.

(c)

1-(3'-Trifluoromethanesulphonamido-4',6'-dimethyl-phenyl)piperidin-2-one 31 g (0.11 mol) of trifluoromethanesulphonic acid anhydride are added dropwise in the course of 40 minutes, at −40°, to a solution of 21.8 g (0.1 mol) of 1-(3'-amino-4',6'-dimethyl-phenyl)-piperidin-2-one and 12 g (0.11 mol) of triethylamine in 400 ml of chloroform. The temperature is allowed to rise to room temperature and the mixture is heated briefly to the reflux temperature. The solution is extracted with 500 ml of 1 N KOH. The aqueous extract is filtered and acidified with concentrated hydrochloric acid. The product thus precipitated is filtered off and washed with water. It is dried in a desiccator at 70°. Yield: 18.0 g (51%); melting point 260°–266°.

The product has the formula

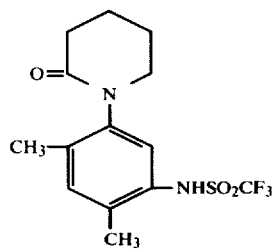

The diethanolamine salt of this compound is a viscous oil.

EXAMPLE 3

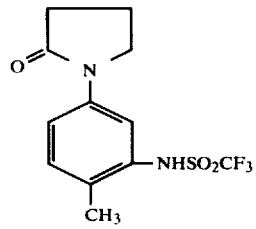

1-(3'-Trifluoromethanesulphonamido-4'-methyl-phenyl)-pyrrolidin-2-one.

31 g (0.11 mol) of trifluoromethanesulphonic acid anhydride are added dropwise in the course of 40 minutes, at −40°, to a solution of 19.0 g (0.1 mol) of 1-(3'-amino-4'-methyl-phenyl)-pyrrolidin-2-one and 12 g of triethylamine in 200 ml of chloroform. The temperature is allowed to rise to room temperature and the mixture is heated briefly to the reflux temperature. The solution is extracted with 350 ml of 1 N KOH solution. The aqueous extract is filtered and acidified with concentrated hydrochloric acid. The product precipitated in this way is filtered off and washed with water. It is dried in a desiccator at 70°. Yield: 16.7 g (52%); melting point 140°–144°.

The corresponding diethanolamine salt is a viscous oil.

EXAMPLE 4

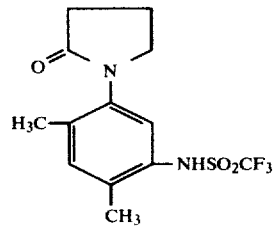

1-(3'-Trifluoromethanesulphonamido-4',6'-dimethyl-phenyl)-pyrrolidin-2-one.

30 g (0.106 mol) of trifluoromethanesulphonic acid anhydride are added dropwise in the course of 40 minutes, at −40°, to a solution of 20.4 g (0.1 mol) of 1-(3'-amino-4',6'-dimethylphenyl)-pyrrolidin-2-one and 12 g (0.11 mol) of triethylamine in 200 ml of chloroform. The temperature is allowed to rise to room temperature and the mixture is then heated briefly to the reflux temperature. The solution is extracted with 1 N KOH solution. The aqueous extract is filtered and acidified with concentrated hydrochloric acid. The product precipitated in this way is filtered off and washed with water. It is dried in a desiccator at 70°. Yield: 16.4 g (49%). Melting point 217°–221°.

The diethanolamine salt is a viscous oil.

EXAMPLE 5

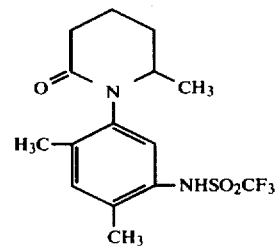

(a)

1-(3'-Amino-4',6'-dimethylphenyl)-6-methyl-piperidin-2-one.

A solution of 65 g (0.5 mol) of 5-oxo-caproic acid and 70 g (0.51 mol) of 3-amino-4,6-dimethylaniline in 300 ml of methanol is hydrogenated at 130°–140° in the presence of Raney nickel. Yield: 110 g.

(b)

The conversion of this amine to the end product, i.e. 1-(3'-trifluoromethanesulphonamido-4',6'-dimethyl-phenyl)-6-methyl-piperidin-2-one is carried out as described in Examples 3 and 4.

EXAMPLE 6

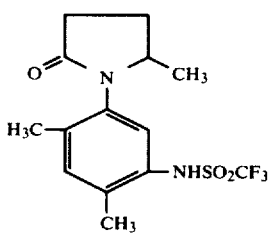

(a) 1-(3'-Amino-4',6'-dimethylphenyl)-5-methyl-pyrrolidin-2-one.

A suspension of 0.2 g of platinum oxide in 25 ml of ethanol is treated with hydrogen and a solution of 34.8 g (0.3 mol) of levulinic acid and 85 g (0.62 mol) of 3-amino-4,6-dimethylaniline in 300 ml of ethanol is then added. The hydrogenation is carried out at room temperature. The desired pyrrolidinone derivative is obtained in a yield of about 80%.

(b)

The conversion to the end product, i.e. 1-(3'-trifluoromethanesulphonamido-4',6'-dimethylphenyl)-5-methyl-pyrrolidin-2-one is carried out analogously to the preceding examples.

EXAMPLE 7

(a) 1,3-Dichloro-4,6-dinitrobenzene 190 ml of fuming nitric acid are added dropwise at 75° C. to a solution of 58.8 g (0.4 mol) of 1,3-dichlorobenzene in 150 ml of trifluoroacetic acid. After 7 hours, the mixture is poured onto ice/water and the product is allowed to crystallise out. The product obtained in this way is filtered off, washed with water and recrystallised from hexane/toluene. Yield: 44 g; melting point 98°-100° C.

(b) 1,3-Dichloro-4,6-diaminobenzene 87.0 g (0.37 mol) of 1,3-dichloro-4,6-dinitrobenzene are dissolved in 1.5 liters of dioxane and, after adding a total of 100 g of Raney Ni, hydrogenated at 40° to 80° C. The catalyst is filtered off and washed with dioxane and the filtrate is concentrated. The product obtained in this way is recrystallised from hexane/toluene. Yield: 40.6 g; melting point 138°-141° C.

(c) N-(3-Amino-4,6-dichlorophenyl)-γ-chlorobutyramide 14.1 g (0.10 mol) of γ-chlorobutyryl chloride in 50 ml of chloroform are added dropwise in the course of 1 hour, at 10°-15° C., to a solution of 17.7 g (0.10 mol) of 1,3-diamino-4,6-dichlorobenzene and 8.7 g (0.11 mol) of pyridine in 500 ml of chloroform. The mixture is then stirred for 2 hours at room temperature, the solution is washed with water and filtered through 40 g of silica gel and the filtrate is concentrated. The resulting product is recrystallised from hexane/toluene. Yield: 13.5 g; melting point 125°-128° C.

(d) 1-(3'-Amino-4',6'-dichlorophenyl)-pyrrolidin-2-one 13.5 g (0.05 mol) of N-(3-amino-4,6-dichlorophenyl)-γ-chlorobutyramide, 200 ml of tetrahydrofurane and 100 ml of 1 N NaOH solution are stirred for 5 hours at 50° C. After the mixture has been allowed to cool, it is extracted three times with 300 ml of ethyl acetate and the extracts are washed with water, dried with magnesium sulphate and concentrated. The resulting product is recrystallised from toluene/ethyl acetate. Yield: 8.5 g; melting point 168°-170° C.

(e) 1-(3'-Trifluoromethanesulphonamido-4',6'-dichlorophenyl)-pyrrolidin-2-one 4.84 g (0.035 mol) of ground potassium carbonate are added to a solution of 7.0 g (0.0286 mol) of 1-(3'-amino-4',6'-dichlorophenyl)-pyrrolidin-2-one in 100 ml of methylene chloride. 9.87 g (0.035 mol) of trifluoromethanesulphonic acid anhydride in 20 ml of methylene chloride are then added dropwise at 0° C., with good stirring. After the addition, the reaction mixture is stirred for a further 30 minutes at the same temperature and then partitioned between methylene chloride and saturated sodium carbonate solution (ice).

The methylene chloride phase is separated off and the aqueous phase is poured onto ice/hydrochloric acid. The end product, which has thus precipitated, is filtered off, washed with water and dried. Yield: 7.47 g; melting point 200°-201° C.

EXAMPLE 8

1-(3'-Trifluoro-methanesulphonamido-4'-chloro-6'-methyl-phenyl)-pyrrolidin-2-one 54.4 ml (0.33 mol) of trifluoromethanesulphonic acid anhydride in 50 ml of chloroform are added dropwise in the course of 1 hour, at 0° C., to a solution of 59.0 g (0.26 mol) of 1-(3'-amino-4'-chloro-6'-methyl-phenyl)-pyrrolidin-2-one and 41.5 ml (0.33 mol) of N,N-dimethylaniline in 600 ml of chloroform. The temperature is then allowed to rise to room temperature and the mixture is stirred for 5 hours. The solution is extracted with 1 N NaOH solution. The aqueous extract is filtered and the filtrate is acidified with concentrated hydrochloric acid. The product precipitated in this way is filtered off and washed with water. It is dried in a desiccator at 70° C. Yield: 32.0 g; melting point 217°-221° C.

EXAMPLE 9

(a) 1-(3'-Amino-4',6'-dimethylphenyl)-piperidine 6.2 g of lithium aluminium hydride are introduced into 200 ml of absolute tetrahydrofurane. 26 g (0.12 mol) of 1-(3'-amino-4',6'-dimethylphenyl)-piperidin-2-one are added in portions, with stirring. The mixture is then refluxed for 1 hour. Excess LiAlH$_4$ is destroyed with ethyl acetate. 2 N HCl is added to the mixture until the pH is 4-5, ether is added and the mixture is extracted twice with 2 N KOH solution. The organic phase is washed with water and saturated NaCl solution, dried with MgSO$_4$, clarified with active charcoal and evaporated. The residue is distilled in a bulb tube. This gives 18.2 g (73%) of a yellow oil (boiling point 140°/0.001 mm Hg).

$C_{13}H_{20}N_2$ [204.32]; calculated: C 76.42; H 9.87; N 13.71%; found: C 76.8; H 9.9; N 14.0%.

(b) 1-(3'-Trifluoromethanesulphonamido-4',6'-dimethylphenyl)-piperidine 20.5 g (0.073 mol) of trifluoromethanesulphonic acid anhydride are added dropwise, at −5° C., to a solution of 13.5 g (0.0664 mol) of 1-(3'-amino-4',6'-dimethylphenyl)-piperidine and 8 g of triethylamine in 140 ml of methylene chloride. The mixture is allowed to warm to room temperature and is stirred for a further one hour. The reaction solution is extracted twice with 1 N KOH solution. The inorganic phase is washed with CHCl$_3$ and filtered and the pH of the filtrate is adjusted to 4-5 with concentrated HCl solution. The product is extracted with CHCl$_3$ and the extract is dried (MgSO$_4$) and evaporated. 5.3 g (24%) of dirty yellow crystals are isolated. Melting point 92°–94° C.

C$_{14}$H$_{19}$F$_3$N$_2$O$_2$S [336.37]; calculated: C 49.99; H, 5.69; N 8.33; S 9.53; F 16.95%; found: C 49.5; H 5.8; N 8.4; S 9.9; F 17.2%.

EXAMPLE 10

(a)

N-(3'-Amino-4'-methylphenyl)-2,3-dimethyl-maleimide of the formula

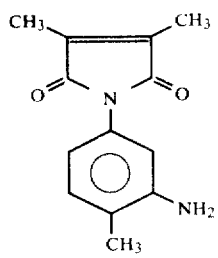

22.8 g (0.15 mol) of 4-amino-2-nitrotoluene and 18.9 g (0.15 mol) of 2,3-dimethylmaleic acid anhydride are heated at 130° C. for 1 hour, while water distils off. The cooled reaction product is recrystallised from methanol [28.6 g (73%); melting point 176° C.] and reduced with H$_2$/Raney Ni in methanol to give the amino compound (24.3 g (96%); melting point 166°–167° C.).

(b)

N-(3'-Trifluoromethanesulphonamido-4'-methylphenyl)-2,3-dimethylmaleimide 9.1 g (1.1 equivalents) of trifluoromethanesulphonic acid anhydride are added dropwise, at −10° C., to 6.8 g (0.0295 mol) of the amine obtained according to (a) and 4 g (1.3 equivalents) of triethylamine, dissolved in 100 ml of methylene chloride. After 45 minutes, the temperature is allowed to rise to room temperature. The reaction solution is extracted with 1 N NaOH. The basic extract is then acidified with concentrated hydrochloric acid and the product which has precipitated is filtered off immediately. After drying at 70° in a vacuum desiccator, 0.5 g of the desired end product with a melting point of 152°–154° is obtained.

EXAMPLE 11

(a) N-Cyanoacetyl-2,4-dimethyl-5-nitroaniline

To a solution of 76.6 g (0.455 mol) of 2,4-dimethyl-5-nitroaniline and 64 ml (0.46 mol) triethylamine in 500 ml abs. tetrahydrofurane is added dropwise within 1 h 47.2 g (0.455 mol) cyanoacetyl chloride in 100 ml tetrahydrofurane. After stirring for 2 h at 25° C. and 3 h at 80° C. and cooling to 25° C. the reaction mixture is filtered and poured into water. The precipitate is separated, washed with water and toluene/petrolether and dried. Yield: 84 g (78%) N-cyanoacetyl-2,4-dimethyl-5-nitroaniline, mp. 229°–230° C.

(b)

1-(3'-Nitro-4',6'-dimethylphenyl)-3-cyano-4,6-dimethyl-2-pyridone

A mixture of 69.2 g (0.30 ml) N-cyanoacetyl-2,4-dimethyl-5-nitroaniline, 31 ml acetylacetone, 15 ml piperidine and 600 ml ethanol are refluxed for 3 h. Upon cooling the 82.5 g (92.5%) 1-(3'-nitro-4',6'-dimethylphenyl)-3-cyano-4,6-dimethyl-2-pyridone cristallise, mp. 262°–263° C.

(c)

1-(3'-Amino-4,6'-dimethylphenyl)-3-cyano-4,6-dimethyl-2-pyridone 48.3 g (0.165 mol) 1-(3'-nitro-4',6'-dimethylphenyl)-3-cyano-4,6-dimethyl-2-pyridone are dissolved in 1 liter of dimethylformamide and, after adding of 5 g palladium/charcoal catalyst, hydrogenated at normal pressure and 15°–20° C. The catalyst is filtered off and the filtrate is concentrated by evaporation. The residue is treated with hexane and dried. Yield: 42.0 g (95.3%) 1-(3'-amino-4',6'-dimethylphenyl)-3-cyano-4,6-dimethyl-2-pyridone, mp. 218°–219° C.

(d)

1-(3-Trifluoromethanesulfonamido-4',6'-dimethylphenyl)-3-cyano-4,6-dimethyl-2-pyridone To a solution of 21.6 g (0.08 mol) 1-(3'-amino-4',6'-dimethylphenyl)-3-cyano-4,6-dimethyl-2-pyridone and 10.4 ml N,N-dimethylaniline in 600 ml of abs. chloroform at 0° C. is added dropwise within 30 minutes a solution of 14.8 ml trifluoromethanesulfonic acid anhydride in 40 ml chloroform. After stirring the solution for 2 h, while the temperature allowed to rise to 25° C., 50 ml of 1 N sodium hydroxid solution is added dropwise. During the latter operation the temperature is controlled by cooling with ice. After separation of the aqueous phase the chloroform solution is once more extracted with 50 ml of 1 N sodium hydroxid solution. The combined aqueous extracts are treated with charcoal, filtrated and acidified with 15 ml of concentrated hydrochloric acid. The precipitating 1-(3'-trifluoromethanesulfonamido-4',6'-dimethylphenyl)-3-cyano-4,6-dimethyl-2-pyridone is separated and dried. Yield: 31.2 g (97.3% of the theory), mp. 274°–276° C.

EXAMPLE 12

1-(3'-trifluoromethanesulfonamido-4',6'-dimethylphenyl)-3-carboxyl-4,6-dimethyl-2-pyridone A mixture of 16.0 g (0.04 mol) 1-(3'-trifluoromethanesulfonamido-4',6'-dimethylphenyl)-3-cyano-4,6-dimethyl-2-pyridone, 24 ml water and 40 ml of concentrated sulfuric acid are refluxed for 8 h. The precipitate that is formed upon pouring the mixture onto ice/water is collected, washed with water, recristallised from ethanol/water and dried. Yield: 14.5 g (86.7%) 1-(3'-trifluoromethanesulfonamido-4',6'-dimethylphenyl)-3-carboxyl-4,6-dimethyl-2-pyridone, mp. 225° C.

EXAMPLE 13

(a)

1-(3'-Nitro-4',6'-dimethylphenyl)-5-chloro-3-methoxycarbonyl-2-methyl-4-pyridone A solution of 10.1 g (0.05 mol) 5-chloro-3-methoxycarbonyl-2-methyl-4-pyranone, 8.5 g 2,4-dimethyl-5-nitroaniline and 0.1 g p-toluenesulfonic acid monohydrate in 100 ml of toluene are refluxed for 8 h in a water separator apparatus. The mixture is allowed to cool and the precipitating product is filtered off, washed with a small amount of ethylacetate/petrolether and dried. Yield: 15.0 g (85.5%) 1-(3'-nitro-4',6'-dimethylphenyl)-5-chloro-3-methoxycarbonyl-2-methyl-4-pyridone, mp. 266° C.

(b)
1-(3'-Amino-4'6'-dimethylphenyl)-5-chloro-3-methoxycarbonyl-2-methyl-4-pyridone 14.7 g (0.042 mol) 1-(3'-nitro-4',6'-dimethylphenyl)-5-chloro-3-methoxycarbonyl-2-methyl-4-pyridone are dissolved in 450 ml dimethylformamide and, after adding of 1.5 g Raney-Ni hydrogenated at normal pressure and 20°-25° C. The catalyst is filtered off and the filtrate is concentrated by evaporation of the solvent. Cristallisation of the residue from ethanol yields 13.2 g (98%) 1-(3'-amino-4',6'-dimethylphenyl)-5-chloro-3-methoxycarbonyl-2-methyl-4-pyridone, mp. 215° C.

(c)
1-(3'-Trifluoromethanesulfonamido-4',6'-dimethylphenyl)-5-chloro-3-methoxycarbonyl-2-methyl-4-pyridone To a solution of 9.6 g (0.03 mol) 1-(3'-amino-4',6'-dimethylphenyl)-5-chloro-3-methoxycarbonyl-2-methyl-4-pyridone and 4.2 ml (0.033 mol) N,N-dimethylaniline in 200 ml of abs. chloroform at 0° C. is added dropwise within 30 minutes a solution of 9.3 g (0.033 mol) trifluoromethanesulfonic acid anhydride in 20 ml of abs. chloroform. After stirring the solution for 3 h at 0°-5° C. and 16 h, while the temperature is allowed to rise to 25° C., 100 ml of water are added. The organic phase is separated, washed with 1 N hydrochloric acid, water and saturated sodium chloride solution, dried with manganese sulfate, filtrated and concentrated by evaporation of the solvent. Cristallisation of the residue from ethanol/water yields 12.8 g (97%) 1-(3'-Trifluoromethanesulfonamido-4',6'-dimethylphenyl)-5-chloro-3-methoxycarbonyl-2-methyl-4-pyridone, mp. 140° C. (dec.).

The tables which follow list novel intermediates and active compounds, according to the invention, of the formula I, the list including compounds which have already been mentioned and also further products prepared according to the invention.

TABLE I

Intermediates

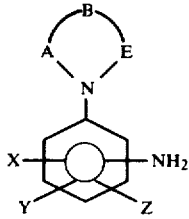

| | Melting point |
|---|---|
| 1-(3'-Amino-4'-methylphenyl)-azetidin-2-one | 161–162° |
| 1-(3'-Amino-4',6'-dimethylphenyl)-azetidin-2-one | 123–124° |
| 1-(3'-Amino-4'-methylphenyl)-pyrrolidin-2-one | 137–141° |
| 1-(3'-Amino-4',6'-dimethylphenyl)-pyrrolidin-2-one | 172–173° |
| 1-(3'-Amino-4',6'-dimethylphenyl)-5-methyl-pyrrolidin-2-one | 156–157° |
| 1-(3'-Amino-4'-methylphenyl)-5-methyl-pyrrolidin-2-one | 110–111° |
| 1-(3'-Amino-4',6'-dimethylphenyl)-piperidin-2-one | 133–135° |
| 1-(3'-Amino-4',6'-dimethylphenyl)-6-methyl-piperidin-2-one | |
| 1-(3'-Amino-4',6'-dimethylphenyl)-3-methyl-pyrrolidin-2-one | viscous |
| 1-(3'-Amino-4',6'-dimethylphenyl)-4-methyl-pyrrolidin-2-one | |
| 1-(3'-Amino-4',6'-dimethylphenyl)-3,5-dimethyl-pyrrolidin-2-one | |
| 1-(3'-Amino-4',6'-dimethylphenyl)-5-n-butyl-pyrrolidin-2-one | |
| 1-(3'-Amino-4',6'-dimethylphenyl)-3,3-dichloro-pyrrolidin-2-one | |
| 1-(3'-Amino-4'-methylphenyl)-3,3-dichloro-pyrrolidin-2-one | |
| 1-(3'-Amino-4',6'-dimethylphenyl)-3-chloro-pyrrolidin-2-one | |
| 1-(3'-Amino-4',6'-dimethylphenyl)-3-cyano-pyrrolidin-2-one | |
| 1-(3'-Amino-4'-methylphenyl)-3-cyano-pyrrolidin-2-one | |
| 1-(3'-Amino-4',6'-dimethylphenyl)-3,3-dimethyl-pyrrolidin-2-one | |
| 1-(3'-Amino-4',6'-dimethylphenyl)-3-ethyl-pyrrolidin-2-one | viscous |
| 1-(3'-Amino-4',6'-dimethylphenyl)-3-methoxy-pyrrolidin-2-one | |
| 1-(3'-Amino-4'-methylphenyl)-piperidin-2-one | 133–134° |
| 1-(3'-Amino-4'-methylphenyl)-3,3-dimethyl-piperidin-2-one | |
| 1-(3'-Amino-4',6'-dimethylphenyl)-4-methyl-piperidin-2-one | |
| 1-(3'-Amino-4',6'-dimethylphenyl)-5-methyl-piperidin-2-one | |
| 1-(3'-Amino-4',6'-dimethylphenyl)-3,3-dimethyl-piperidin-2-one | |
| 1-(3'-Amino-4',6'-dimethylphenyl)-6-n-pentyl-piperidin-2-one | |
| 1-(3'-Amino-4',6'-dimethylphenyl)-4-isopropyl-piperidin-2-one | |
| 1-(3'-Amino-4',6'-dimethylphenyl)-3,3-dichloro-piperidin-2-one | |
| 1-(3'-Amino-4',6'-dimethylphenyl)-3-chloro-piperidin-2-one | |
| 1-(3'-Amino-4',6'-dimethylphenyl)-5-chloro-piperidin-2-one | |
| 1-(3'-Amino-4',6'-dimethylphenyl)-5-cyano-piperidin-2-one | |
| 1-(3'-Amino-4',6'-dimethylphenyl)-3-methoxy-piperidin-2-one | |
| 1-(3'-Amino-2'-methylphenyl)-pyrrolidin-2-one | 170–171° |
| 1-(3'-Amino-6'-methylphenyl)-pyrrolidin-2-one | 138–140° |
| 1-(3'-Amino-2',6'-dimethylphenyl)-pyrrolidin-2-one | 148–151° |
| 1-(3'-Amino-2',4'-dimethylphenyl)-pyrrolidin-2-one | 217–218° |
| 1-(2'-Amino-4',5'-dimethylphenyl)-pyrrolidin-2-one | 152–154° |
| 1-(3'-Amino-2'-methylphenyl)-piperidin-2-one | |
| 1-(3'-Amino-6'-methylphenyl)-piperidin-2-one | |
| 1-(3'-Amino-2',6'-dimethylphenyl)-piperidin-2-one | |
| 1-(3'-Amino-2',4'-dimethylphenyl)-piperidin-2-one | |
| 1-(2'-Amino-4',5'-dimethylphenyl)-piperidin- | |

TABLE I-continued

Intermediates

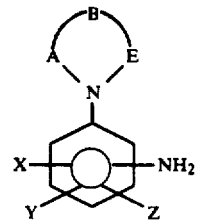

TABLE I-continued

Intermediates

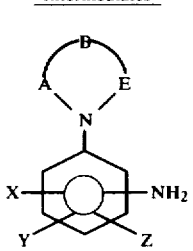

| | Melting point |
|---|---|
| 2-one | |
| 1-(3'-Amino-4'-ethylphenyl)-pyrrolidin-2-one | 105–106° |
| 1-(3'-Amino-4'-ethylphenyl)-piperidin-2-one | |
| 1-(3'-Amino-4',5'-dimethylphenyl)-pyrrolidin-2-one | 145–147° |
| 1-(3'-Amino-2',6'-diethylphenyl)-pyrrolidin-2-one | 142–143° |
| 1-(3'-Amino-2',6'-diethylphenyl)-piperidin-2-one | |
| 1-(3'-Amino-2',4',6'-trimethylphenyl)-pyrrolidin-2-one | 129–133° |
| 1-(3'-Amino-2',4',6'-trimethylphenyl)-piperidin-2-one | |
| 1-(3'-Amino-2'-methyl-6'-t-butylphenyl)-pyrrolidin-2-one | |
| 1-(3'-Amino-2'-methyl-6'-t-butylphenyl)-piperidin-2-one | |
| 1-(3'-Amino-4',6'-diethylphenyl)-pyrrolidin-2-one | |
| 1-(3'-Amino-4',6'-diethylphenyl)-piperidin-2-one | |
| 1-(3'-Amino-4'-t-butylphenyl)-pyrrolidin-2-one | |
| 1-(3'-Amino-4'-t-butylphenyl)-piperidin-2-one | |
| 1-(3'-Amino-2'-methyl-5'-isopropylphenyl)-pyrrolidin-2-one | |
| 1-(3'-Amino-2'-methyl-5'-isopropylphenyl)-piperidin-2-one | |
| 1-(3'-Amino-2'-ethylphenyl)-pyrrolidin-2-one | |
| 1-(3'-Amino-2'-ethylphenyl)-piperidin-2-one | |
| 1-(3'-Amino-4'-isopropylphenyl)-pyrrolidin-2-one | |
| 1-(3'-Amino-4'-isopropylphenyl)-piperidin-2-one | |
| 1-(3'-Amino-4'-n-butylphenyl)-pyrrolidin-2-one | |
| 1-(3'-Amino-4'-n-butylphenyl)-piperidin-2-one | |
| 1-(3'-Amino-4'-chlorophenyl)-pyrrolidin-2-one | 135–137° |
| 1-(3'-Amino-4'-chlorophenyl)-piperidin-2-one | 125° |
| 1-(3'-Amino-4'-chloro-6'-methylphenyl)-pyrrolidin-2-one | 171–173° |
| 1-(3'-Amino-4'-chloro-6'-methylphenyl)-piperidin-2-one | 158° |
| 1-(3'-Amino-phenyl)-pyrrolidin-2-one | 105° |
| 1-(3'-Amino-phenyl)-piperidin-2-one | 135–140° |
| 1-(3'-Amino-4'-fluorophenyl)-pyrrolidin-2-one | 103–105° |
| 1-(3'-Amino-4'-fluorophenyl)-piperidin-2-one | |
| 1-(3'-Amino-6'-methoxyphenyl)-pyrrolidin-2-one | 101–103° |
| 1-(3'-Amino-4'-methoxyphenyl)-piperidin-2-one | 104° |
| 1-(3'-Amino-4',6'-dichlorophenyl)-pyrrolidin-2-one | 168–170° |
| 1-(3'-Amino-4',6'-dichlorophenyl)-piperidin-2-one | |
| 1-(3'-Amino-2',4'-diethylphenyl)-pyrrolidin-2-one | 147–149° |
| 1-(3'-Amino-2',4'-diethylphenyl)-piperidin-2-one | |
| 1-(3'-Amino-5'-chloro-6'-methoxyphenyl)-pyrrolidin-2-one | |
| 1-(3'-Amino-5'-chloro-6'-methoxyphenyl)-piperidin-2-one | |
| 1-(3'-Amino-2'-methyl-6'-chlorophenyl)-pyrrolidin-2-one | |
| 1-(3'-Amino-2'-methyl-6'-chlorophenyl)-piperidin-2-one | |
| 1-(3'-Amino-4'-methoxyphenyl)-pyrrolidin-2-one | 118° |
| 1-(3'-Amino-4'-methoxyphenyl)-piperidin-2-one | |
| 1-(3'-Amino-4',6'-dimethoxyphenyl)-pyrrolidin-2-one | |
| 1-(3'-Amino-4',6'-dimethoxyphenyl)-piperidin-2-one | |
| 1-(4'-Amino-phenyl)-pyrrolidin-2-one | |
| 1-(4'-Amino-phenyl)-piperidin-2-one | |
| 1-(4'-Amino-2'-trifluoromethylphenyl)-pyrrolidin-2-one | |

TABLE I-continued

Intermediates

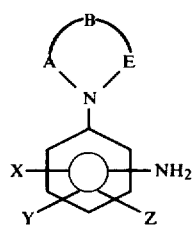

| | Melting point |
|---|---|
| 2-one | 148° |
| 1-(4'-Amino-3'-methylsulphonyl-6'-methoxyphenyl)-piperidin-2-one | |
| 1-(4'-Amino-2'-trifluoromethylphenyl)-piperidin-2-one | |
| 1-(4'-Amino-3'-methylsulphonyl-6'-methoxyphenyl)-pyrrolidin-2-one | |
| 1-(4'-Amino-3'-chloro-6'-methoxyphenyl)-pyrrolidin-2-one | |
| 1-(4'-Amino-3'-chloro-6'-methoxyphenyl)-piperidin-2-one | |
| 1-(4'-Amino-2'-chlorophenyl)-pyrrolidin-2-one | |
| 1-(4'-Amino-2'-chlorophenyl)-piperidin-2-one | |
| 1-(4'-Amino-2'-ethoxycarbonylphenyl)-pyrrolidin-2-one | |
| 1-(4'-Amino-2'-ethoxycarbonylphenyl)-piperidin-2-one | |
| 1-(4'-Amino-3'-ethoxycarbonylphenyl)-pyrrolidin-2-one | |
| 1-(4'-Amino-3'-ethoxycarbonylphenyl)-piperidin-2-one | |
| 1-(4'-Amino-2'-methyl-5'-chlorophenyl)-pyrrolidin-2-one | |
| 1-(4'-Amino-2'-methyl-5'-chlorophenyl)-piperidin-2-one | |
| 1-(2'-Amino-phenyl)-pyrrolidin-2-one | 92–94° |
| 1-(2'-Amino-4'-ethylsulphonyl-phenyl)-pyrrolidin-2-one | |
| 1-(2'-Amino-4'-ethylsulphonyl-phenyl)-piperidin-2-one | |
| 1-(2'-Amino-4'-chlorophenyl)-pyrrolidin-2-one | |
| 1-(2'-Amino-4'-chlorophenyl)-piperidin-2-one | |
| 1-(2'-Amino-5'-methyl-6'-chlorophenyl)-pyrrolidin-2-one | |
| 1-(2'-Amino-5'-methyl-6'-chlorophenyl)-piperidin-2-one | |
| 1-(3'-Amino-4'-[2,4-dichlorophenoxy]-phenyl)-pyrrolidin-2-one | |
| 1-(3'-Amino-4'-[2,4-dichlorophenoxy]-phenyl)-piperidin-2-one | |
| 1-(3'-Amino-4'-[4-trifluoromethylphenoxy]-phenyl)-pyrrolidin-2-one | |
| 1-(3'-Amino-4'-[4-trifluoromethylphenoxy]-phenyl)-piperidin-2-one | |
| 1-(3'-Amino-4'-[2,4-dichlorobenzyl]-phenyl)-pyrrolidin-2-one | |
| 1-(3'-Amino-4'-[2,4-dichlorobenzyl]-phenyl)-piperidin-2-one | |
| 1-(3'-Amino-4',6'-dimethylphenyl)-azetidine | viscous |
| 1-(3'-Amino-4'-methylphenyl)-pyrrolidine | 59–68° |
| 1-(3'-Amino-4',6'-dimethylphenyl)-pyrrolidine | boiling point 130°/0.1 |
| 1-(3'-Amino-4'-methylphenyl)-piperidine | boiling point 155°/0.005 |
| 1-(3'-Amino-4',6'-dimethylphenyl)-piperidine | boiling point 140°/0.001 |
| 1-(3'-Amino-4',6'-dimethylphenyl)-pyrrolidine-2,5-dione | melting point 230–232° |
| 1-(3'-Amino-5',6'-dimethylphenyl)-pyrrolidin-2-one | 172–174° |
| 1-(3'-Amino-5'-methylphenyl)-pyrrolidin-2-one | 117–119° |
| 1-(2'-Amino-5',6'-dimethylphenyl)-pyrrolidin-2-one | 153–155° |
| 1-(2'-Amino-4'-methylphenyl)-pyrrolidin-2-one | 100–103° |
| 1-(4'-Amino-2'-methyl-5'-chlorophenyl)-pyrrolidin-2-one | 148–150° |
| 1-(4'-Amino-2'-methoxy-phenyl)-pyrrolidin- | |

TABLE 1-continued

Intermediates structure: ring with A-B-E-N attached to benzene ring bearing NH2, X, Y, Z substituents

| | Melting point |
|---|---|
| 2-one | 126–127° |
| 1-(3'-Amino-4',5'-dimethylphenyl)-piperidin-2-one | 135–138° |
| 1-(3'-Amino-4',6'-dimethylphenyl)-hexahydroazepin-2-one | 98–99° |
| 1-(3'-Amino-4'-methylphenyl)-hexahydroazepine | boiling point 130°/0.01 mm Hg |
| 1-(3'-Amino-4',6'-dimethylphenyl)-hexahydroazepine | boiling point 130°/0.04 mm Hg |
| 1-(3'-Amino-4'-methylphenyl)-3,4-dimethyl-2,5-dihydro-pyrrole-2,5-dione | 166–167° |
| 1-(3'-Amino-4'-methylphenyl)-3-methyl-pyrrolidin-2-one | 96–100° |
| 1-(3'-Amino-4'-methylphenyl)-3-ethyl-pyrrolidin-2-one | |
| 1-(3'-Amino-4'-methylphenyl)-5-butyl-pyrrolidin-2-one | |
| 1-(3'-Amino-4'-methylphenyl)-4,5-dimethyl-pyrrolidin-2-one | |
| 1-(3'-Amino-4',6'-dimethylphenyl)-4,5-dimethyl-pyrrolidin-2-one | |
| 1-(3'-Amino-4',6'-dimethylphenyl)-3,5-dimethyl-pyrrolidin-2-one | |
| 1-(3'-Amino-4'-methylphenyl)-3,5-dimethyl-pyrrolidin-2-one | |
| 1-(3'-Amino-4'-methylphenyl)-3-propyl-pyrrolidin-2-one | |
| 1-(3'-Amino-4',6'-dimethylphenyl)-3-propyl-pyrrolidin-2-one | |
| 1-(3'-Amino-4'-methylphenyl)-3-butyl-pyrrolidin-2-one | |
| 1-(3'-Amino-4',6'-dimethylphenyl)-3-butyl-pyrrolidin-2-one | |
| 1-(3'-Amino-4'-methylphenyl)-5-ethyl-pyrrolidin-2-one | |
| 1-(3'-Amino-4',6'-dimethylphenyl)-5-ethyl-pyrrolidin-2-one | |
| 1-(3'-Amino-4'-methylphenyl)-5-octyl-pyrrolidin-2-one | |
| 1-(3'-Amino-4',6'-dimethylphenyl)-5-octyl-pyrrolidin-2-one | |
| 1-(3'-Amino-4'-methylphenyl)-3-isobutyl-pyrrolidin-2-one | |
| 1-(3'-Amino-4',6'-dimethylphenyl)-3-isobutyl-pyrrolidin-2-one | |
| 1-(3'-Amino-phenyl)-3-methyl-pyrrolidin-2-one | |
| 1-(3'-Amino-4',5'-dimethylphenyl)-3-methyl-pyrrolidin-2-one | 121–125° |
| 1-(3'-Amino-6'-methylphenyl)-3-methyl-pyrrolidin-2-one | 110–113° |
| 1-(3'-Amino-4'-chloro-6'-methylphenyl)-3-methyl-pyrrolidin-2-one | |
| 1-(3'-Amino-4',6'-dichlorophenyl)-3-methyl-pyrrolidin-2-one | |
| 1-(3'-Amino-4'-methoxyphenyl)-3-methyl-pyrrolidin-2-one | |
| 1-(3'-Amino-6'-methoxyphenyl)-3-methyl-pyrrolidin-2-one | |
| 1-(3'-Amino-5'-methylphenyl)-3-methyl-pyrrolidin-2-one | |
| 1-(3'-Amino-4'-chloro-6'-methylphenyl)-3-ethyl-pyrrolidin-2-one | |
| 1-(3'-Amino-phenyl)-5-methyl-pyrrolidin-2-one | |
| 1-(3'-Amino-6'-methylphenyl)-5-methyl-pyrrolidin-2-one | 151–154° |
| 1-(3'-Amino-4',5'-dimethylphenyl)-5-methyl-pyrrolidin-2-one | 105–107° |
| 1-(3'-Amino-4'-chloro-6'-methylphenyl)-5-methyl-pyrrolidin-2-one | |
| 1-(3'-Amino-4',6'-dichlorophenyl)-5-methyl-pyrrolidin-2-one | |
| 1-(3'-Amino-4'-methoxyphenyl)-5-methyl-pyrrolidin-2-one | |
| 1-(3'-Amino-4'-chloro-6'-methylphenyl)-5-butyl-pyrrolidin-2-one | |
| 1-(3'-Amino-4',6'-dichlorophenyl)-5-butyl-pyrrolidin-2-one | |
| 1-(3'-Amino-phenyl)-4,5-dimethyl-pyrrolidin-2-one | |
| 1-(3'-Amino-4'-chloro-6'-methylphenyl)-4,5-dimethyl-pyrrolidin-2-one | |
| 1-(3'-Amino-4',6'-dichlorophenyl)-4,5-dimethyl-pyrrolidin-2-one | |
| 1-(3'-Amino-4'-chloro-6'-methylphenyl)-3,5-dimethyl-pyrrolidin-2-one | |
| 1-(3'-Amino-4'-methoxyphenyl)-3,5-dimethyl-pyrrolidin-2-one | |
| 1-(3'-Amino-4',6'-dichlorophenyl)-3-propyl-pyrrolidin-2-one | |
| 1-(3'-Amino-4'-chloro-6'-methylphenyl)-3-butyl-pyrrolidin-2-one | |
| 1-(3'-Amino-6'-methylphenyl)-5-ethyl-pyrrolidin-2-one | |
| 1-(3'-Amino-4',5'-dimethylphenyl)-5-ethyl-pyrrolidin-2-one | |
| 1-(3'-Amino-4'-chloro-6'-methylphenyl)-5-ethyl-pyrrolidin-2-one | |
| 1-(3'-Amino-4',6'-dichlorophenyl)-5-ethyl-pyrrolidin-2-one | |
| 1-(3'-Amino-4'-methoxyphenyl)-5-ethyl-pyrrolidin-2-one | |
| 1-(3'-Amino-4'-methoxyphenyl)-5-octyl-pyrrolidin-2-one | |
| 1-(3'-Amino-4'-chloro-6'-methylphenyl)-3-isobutyl-pyrrolidin-2-one | |
| 1-(3'-Amino-4'-methylphenyl)-6-methyl-piperidin-2-one | |
| 1-(3'-Amino-4'-methylphenyl)-6-ethyl-piperidin-2-one | |
| 1-(3'-Amino-4'-methylphenyl)-6-ethyl-piperidin-2-one | |
| 1-(3'-Amino-4',6'-dimethylphenyl)-4-isopropyl-piperidin-2-one | |
| 1-(3'-Amino-4'-methylphenyl)-3-methyl-piperidin-2-one | |
| 1-(3'-Amino-4'-methylphenyl)-3-ethyl-piperidin-2-one | |
| 1-(3'-Amino-4',6'-dimethylphenyl)-3-ethyl-piperidin-2-one | |
| 1-(3'-Amino-4'-methylphenyl)-4-methyl-piperidin-2-one | |
| 1-(3'-Amino-4'-methylphenyl)-5-methyl-piperidin-2-one | |
| 1-(3'-Amino-4'-methylphenyl)-6-pentyl-piperidin-2-one | |
| 1-(3'-Amino-4'-methylphenyl)-3,3-dichloro-piperidin-2-one | |
| 1-(3'-Amino-4'-methylphenyl)-3-chloro-piperidin-2-one | |
| 1-(3'-Amino-phenyl)-6-methyl-piperidin-2-one | |
| 1-(3'-Amino-6'-methylphenyl)-6-methyl-piperidin-2-one | |
| 1-(3'-Amino-4',5'-dimethylphenyl)-6- | |

TABLE I-continued

Intermediates

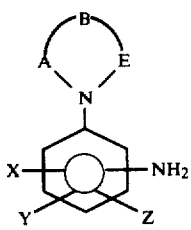

| | Melting point |
|---|---|
| methyl-piperidin-2-one | |
| 1-(3'-Amino-4'-chloro-6'-methylphenyl)-6-methyl-piperidin-2-one | |
| 1-(3'-Amino-4',6'-dichlorophenyl)-6-methyl-piperidin-2-one | |
| 1-(3'-Amino-4'-methoxyphenyl)-6-methyl-piperidin-2-one | |
| 1-(3'-Amino-phenyl)-6-ethyl-piperidin-2-one | |
| 1-(3'-Amino-6'-methylphenyl)-3-methyl-piperidin-2-one | |
| 1-(3'-Amino-4',5'-dimethylphenyl)-3-methyl-piperidin-2-one | |
| 1-(3'-Amino-4'-chloro-6'-methylphenyl)-3-methyl-piperidin-2-one | |
| 1-(3'-Amino-4',6'-dichlorophenyl)-3-methyl-piperidin-2-one | |
| 1-(3'-Amino-4'-methoxyphenyl)-3-methyl-piperidin-2-one | |
| 1-(3'-Amino-phenyl)-3-ethyl-piperidin-2-one | |
| 1-(3'-Amino-6'-methylphenyl)-3-ethyl-piperidin-2-one | |
| 1-(3'-Amino-4',6'-dichlorophenyl)-3-ethyl-piperidin-2-one | |
| 1-(3'-Amino-phenyl)-hexahydro-azepin-2-one | |
| 1-(3'-Amino-4'-methylphenyl)-hexahydro-azepin-2-one | 128–130° |
| 1-(3'-Amino-6'-methylphenyl)-hexahydro-azepin-2-one | |
| 1-(3'-Amino-4',5'-dimethylphenyl)-hexahydro-azepin-2-one | |
| 1-(3'-Amino-4'-chloro-6'-methylphenyl)-hexahydro-azepin-2-one | |
| 1-(3'-Amino-4',6'-dichlorophenyl)-hexahydro-azepin-2-one | |
| 1-(3'-Amino-4'-methoxyphenyl)-hexahydro-azepin-2-one | |
| 1-(3'-Amino-4'-methylphenyl)-3-cyano-4,6-dimethylpyrid-2-one | |
| 1-(3'-Amino-4',6'-dimethylphenyl)-3-cyano-4,6-dimethylpyrid-2-one | |
| 1-(3'-Amino-4'-chlorophenyl)-3-cyano-4,6-dimethylpyrid-2-one | |
| 1-(3'-Amino-4'-methoxyphenyl)-3-cyano-4,6-dimethylpyrid-2-one | |

TABLE I-continued

Intermediates

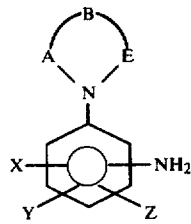

| | Melting point |
|---|---|
| 1-(3'-Amino-phenyl)-3-cyano-4,6-dimethyl-pyrid-2-one | |
| 1-(3'-Amino-4'-methylphenyl)-3-methoxycarbonyl-2,6-dimethyl-pyrid-4-one | |
| 1-(3'-Amino-4',6'-dimethylphenyl)-3-methoxycarbonyl-2,6-dimethyl-pyrid-4-one | |
| 1-(3'-Amino-4'-chlorophenyl)-3-methoxycarbonyl-2,6-dimethyl-pyrid-4-one | |
| 1-(3'-Amino-4'-methoxyphenyl)-3-methoxycarbonyl-2,6-dimethyl-pyrid-4-one | |
| 1-(3'-Amino-phenyl)-3-methoxycarbonyl-2,6-dimethyl-pyrid-4-one | |
| 1-(3'-Amino-4'-methylphenyl)-3-methoxycarbonyl-5-chloro-2-methyl-pyrid-4-one | |
| 1-(3'-Amino-4',6'-dimethylphenyl)-3-methoxycarbonyl-5-chloro-2-methyl-pyrid-4-one | |
| 1-(3'-Amino-4'-chlorophenyl)-3-methoxycarbonyl-5-chloro-2-methyl-pyrid-4-one | |
| 1-(3'-Amino-4'-methoxyphenyl)-3-methoxycarbonyl-5-chloro-2-methyl-pyrid-4-one | |
| 1-(3'-Amino-phenyl)-3-methoxycarbonyl-5-chloro-2-methyl-pyrid-4-one | |

Novel active compounds of the formula I (a) containing a 4-membered ring heterocyclic structure (azetidinones)

TABLE 2

| Compound No. | | Melting point (°C.) |
|---|---|---|
| 1 | 1-(3'-trifluoromethanesulphonamido-4'-methylphenyl)-azetidin-2-one | 140–143° |
| 2 | 1-(3'-trifluoromethanesulphonamido-4',6'-dimethyl-phenyl)-azetidin-2-one | 137–139° |
| 3 | diethanolamine salt of 2 | viscous oil |

(b) containing a 5-membered ring heterocyclic structure (pyrrolidin-2-ones)

TABLE 3a

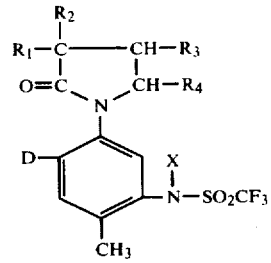

| Compound No. | D | $R_1$ | $R_2$ | $R_3$ | $R_4$ | X | Melting point °C. |
|---|---|---|---|---|---|---|---|
| 4 | H | H | H | H | H | H | 140–144° |
| 5 | H | H | H | H | H | $H_2N^{\oplus}(CH_2CH_2OH)_2$ | viscous oil |
| 6 | $CH_3$ | H | H | H | H | H | 217–221° |
| 7 | $CH_3$ | H | H | H | H | $H_2N^{\oplus}(CH_2CH_2OH)_2$ | viscous oil |

TABLE 3a-continued

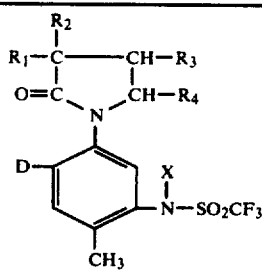

| Compound No. | D | $R_1$ | $R_2$ | $R_3$ | $R_4$ | X | Melting point °C. |
|---|---|---|---|---|---|---|---|
| 8 | $CH_3$ | $CH_3$ | H | H | H | H | 240–241° |
| 9 | $CH_3$ | H | H | $CH_3$ | H | H | 220–224° |
| 10 | $CH_3$ | H | H | H | $CH_3$ | H | 243–245° |
| 11 | $CH_3$ | H | H | H | $CH_3$ | $H_2N^\oplus(CH_2CH_2OH)_2$ | |
| 12 | H | H | H | H | $CH_3$ | H | 137–138° |
| 13 | $CH_3$ | H | $CH_3$ | H | $CH_3$ | H | |
| 14 | $CH_3$ | H | H | H | n-$C_4H_9$ | H | 200–202° |
| 15 | $CH_3$ | Cl | Cl | H | H | H | |
| 16 | H | Cl | Cl | H | H | H | |
| 17 | $CH_3$ | Cl | H | H | H | H | |
| 18 | $CH_3$ | Cl | H | H | H | $H_2N^\oplus(CH_2CH_2OH)_2$ | |
| 19 | $CH_3$ | CN | H | H | H | H | |
| 20 | H | CN | H | H | H | H | |
| 21 | $CH_3$ | $CH_3$ | $CH_3$ | H | H | H | 212–214° |
| 22 | $CH_3$ | $OCH_3$ | H | H | H | H | |
| 23 | $CH_3$ | $C_2H_5$ | H | H | H | H | 194° |
| 24 | H | $CH_3$ | H | H | H | H | 140–144° |
| 25 | H | $C_2H_5$ | H | H | H | H | 134–125° |
| 26 | H | H | H | H | n-$C_4H_9$ | H | |
| 27 | H | H | H | $CH_3$ | $CH_3$ | H | |
| 28 | $CH_3$ | H | H | $CH_3$ | $CH_3$ | H | |
| 29 | $CH_3$ | $CH_3$ | H | H | $CH_3$ | H | |
| 30 | H | $CH_3$ | H | H | $CH_3$ | H | |
| 31 | H | n-$C_3H_7$ | H | H | H | H | |
| 32 | $CH_3$ | n-$C_3H_7$ | H | H | H | H | |
| 33 | H | n-$C_4H_9$ | H | H | H | H | |
| 34 | $CH_3$ | n-$C_4H_9$ | H | H | H | H | |
| 35 | H | H | H | H | $C_2H_5$ | H | |
| 36 | $CH_3$ | H | H | H | $C_2H_5$ | H | |
| 37 | H | H | H | H | n-$C_8H_{17}$ | H | |
| 38 | $CH_3$ | H | H | H | n-$C_8H_{17}$ | H | 130–132° |
| 39 | H | i-$C_4H_9$ | H | H | H | H | |
| 40 | $CH_3$ | i-$C_4H_9$ | H | H | H | H | 198–200° |

TABLE 3b

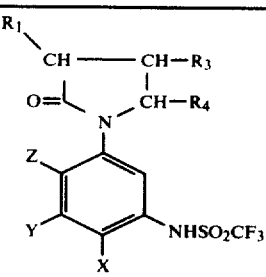

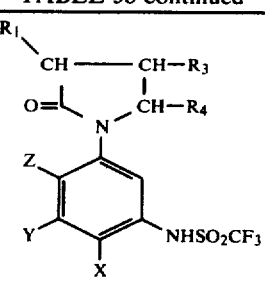

| Compound No. | $R_1$ | $R_3$ | $R_4$ | X | Y | Z | Melting point (°C.) |
|---|---|---|---|---|---|---|---|
| 41 | $CH_3$ | H | H | H | H | H | |
| 42 | $CH_3$ | H | H | $CH_3$ | $CH_3$ | H | 150–155° |
| 43 | $CH_3$ | H | H | H | H | $CH_3$ | 203–206° |
| 44 | $CH_3$ | H | H | Cl | H | $CH_3$ | 227–228° |
| 45 | $CH_3$ | H | H | Cl | H | Cl | |
| 46 | $CH_3$ | H | H | $OCH_3$ | H | H | |
| 47 | $CH_3$ | H | H | H | H | $OCH_3$ | |
| 48 | $CH_3$ | H | H | H | $CH_3$ | H | |
| 49 | $C_2H_5$ | H | H | Cl | H | $CH_3$ | |
| 50 | H | H | H | $CH_3$ | H | H | 126–127° |
| 51 | H | H | $CH_3$ | H | H | $CH_3$ | 198–200° |
| 52 | H | H | $CH_3$ | $CH_3$ | $CH_3$ | H | 170–174° |
| 53 | H | H | $CH_3$ | Cl | H | $CH_3$ | 216–220° |

TABLE 3b-continued

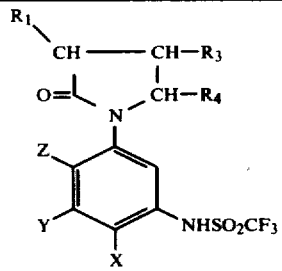

| Compound No. | $R_1$ | $R_3$ | $R_4$ | X | Y | Z | Melting point (°C.) |
|---|---|---|---|---|---|---|---|
| 54 | H | H | $CH_3$ | Cl | H | Cl | |
| 55 | H | H | $CH_3$ | $OCH_3$ | H | H | 167–168° |
| 56 | H | H | $n-C_4H_9$ | Cl | H | $CH_3$ | |
| 57 | H | H | $n-C_4H_9$ | Cl | H | Cl | |
| 58 | H | $CH_3$ | $CH_3$ | H | H | H | |
| 59 | H | $CH_3$ | $CH_3$ | Cl | H | $CH_3$ | |
| 60 | H | $CH_3$ | $CH_3$ | Cl | H | Cl | |
| 61 | $CH_3$ | H | $CH_3$ | Cl | H | $CH_3$ | |
| 62 | $CH_3$ | H | $CH_3$ | $OCH_3$ | H | H | |
| 63 | $n-C_3H_7$ | H | H | Cl | H | Cl | |
| 64 | $n-C_4H_9$ | H | H | Cl | H | $CH_3$ | |
| 65 | H | H | $C_2H_5$ | H | H | $CH_3$ | |
| 66 | H | H | $C_2H_5$ | $CH_3$ | $CH_3$ | H | |
| 67 | H | H | $C_2H_5$ | Cl | H | $CH_3$ | |

TABLE 3b-continued

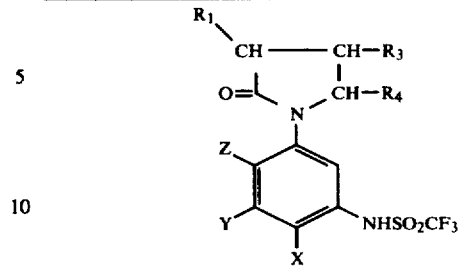

| Compound No. | $R_1$ | $R_3$ | $R_4$ | X | Y | Z | Melting point (°C.) |
|---|---|---|---|---|---|---|---|
| 68 | H | H | $C_2H_5$ | Cl | H | Cl | |
| 69 | H | H | $C_2H_5$ | $OCH_3$ | H | H | |
| 70 | H | H | $n-C_8H_{17}$ | $OCH_3$ | H | H | |
| 71 | $i-C_4H_9$ | H | H | Cl | H | $CH_3$ | |
| 72 | H | H | H | H | $CH_3$ | $CH_3$ | 216–218° |
| 73 | H | H | H | H | $CH_3$ | H | 188–189° |

(c) containing a 6-membered ring heterocyclic structure (piperidin-2-ones)

TABLE 4a

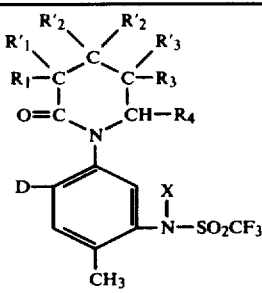

| Compound No. | D | $R_1$ | $R'_1$ | $R_2$ | $R'_2$ | $R_3$ | $R'_3$ | $R_4$ | X | Melting point (°C.) |
|---|---|---|---|---|---|---|---|---|---|---|
| 74 | $CH_3$ | H | H | H | H | H | H | H | H | 260–266° |
| 75 | $CH_3$ | H | H | H | H | H | H | H | $H_2N^{\oplus}(CH_2CH_2OH)_2$ | viscous oil |
| 76 | $CH_3$ | $CH_3$ | H | H | H | H | H | H | H | |
| 77 | $CH_3$ | H | H | $CH_3$ | H | H | H | H | H | |
| 78 | $CH_3$ | H | H | H | H | $CH_3$ | H | H | H | |
| 79 | $CH_3$ | H | H | H | H | H | H | $CH_3$ | H | |
| 80 | $CH_3$ | $CH_3$ | $CH_3$ | H | H | H | H | H | H | |
| 81 | H | $CH_3$ | $CH_3$ | H | H | H | H | H | H | |
| 82 | $CH_3$ | H | H | H | H | H | H | $n-C_5H_{11}$ | H | |
| 83 | $CH_3$ | H | H | H | $i-C_3H_7$ | H | H | H | H | |
| 84 | H | H | H | H | H | H | H | H | H | 172–176° |
| 85 | $CH_3$ | Cl | Cl | H | H | H | H | H | H | |
| 86 | $CH_3$ | Cl | H | H | H | H | H | H | H | |
| 87 | $CH_3$ | H | H | H | H | Cl | H | H | H | |
| 88 | $CH_3$ | H | H | H | H | CN | H | H | H | |
| 89 | $CH_3$ | $-OCH_3$ | H | H | H | H | H | H | H | |
| 90 | H | H | H | H | H | H | H | $CH_3$ | H | |
| 91 | H | H | H | H | H | H | H | $C_2H_5$ | H | |
| 92 | $CH_3$ | H | H | H | H | H | H | $C_2H_5$ | H | |
| 93 | H | $CH_3$ | H | H | H | H | H | H | H | |
| 94 | H | $C_2H_5$ | H | H | H | H | H | H | H | |
| 95 | $CH_3$ | $C_2H_5$ | H | H | H | H | H | H | H | |
| 96 | H | H | H | $CH_3$ | H | H | H | H | H | |
| 97 | H | H | H | H | H | $CH_3$ | H | H | H | |
| 98 | H | H | H | H | H | H | H | $n-C_5H_{11}$ | H | |
| 99 | H | H | H | H | $i-C_3H_7$ | H | H | H | H | |
| 100 | H | Cl | Cl | H | H | H | H | H | H | |
| 101 | H | Cl | H | H | H | H | H | H | H | |

(d) containing a 7-membered ring heterocyclic structure

TABLE 4b

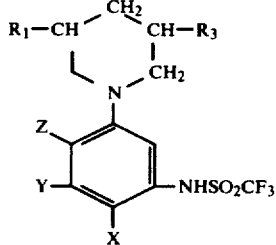

| Compound No. | $R_1$ | $R_3$ | X | Y | Z | Melting point (°C.) |
|---|---|---|---|---|---|---|
| 102 | H | $CH_3$ | H | H | H | |
| 103 | H | $CH_3$ | H | H | $CH_3$ | |
| 104 | H | $CH_3$ | $CH_3$ | $CH_3$ | H | |
| 105 | H | $CH_3$ | Cl | H | $CH_3$ | |
| 106 | H | $CH_3$ | Cl | H | Cl | |
| 107 | H | $CH_3$ | $OCH_3$ | H | H | |
| 108 | H | $C_2H_5$ | H | H | H | |
| 109 | $CH_3$ | H | H | H | $CH_3$ | |
| 110 | $CH_3$ | H | $CH_3$ | $CH_3$ | H | |
| 111 | $CH_3$ | H | Cl | H | $CH_3$ | |
| 112 | $CH_3$ | H | Cl | H | Cl | |
| 113 | $CH_3$ | H | $OCH_3$ | H | H | |
| 114 | $C_2H_5$ | H | H | H | H | |
| 115 | $C_2H_5$ | H | H | H | $CH_3$ | |
| 116 | $C_2H_5$ | H | Cl | H | Cl | |
| 117 | H | H | $CH_3$ | $CH_3$ | H | 200–205° |
| 117a | H | H | H | H | $CH_3$ | 239–244° |

TABLE 5

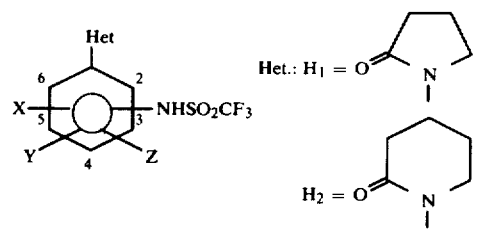

| Compound No. | X | Y | Z | R | Melting point (°C.) |
|---|---|---|---|---|---|
| 118 | H | H | H | H | 147–150° |
| 119 | $CH_3$ | H | H | H | 143–145° |
| 120 | H | H | $CH_3$ | H | 185–188° |
| 121 | $CH_3$ | $CH_3$ | H | H | 197–203° |
| 122 | $CH_3$ | H | $CH_3$ | H | 237–238° |
| 123 | $CH_3$ | H | $CH_3$ | $H_2\overset{\oplus}{N}(CH_2CH_2OH)_2$ | viscous oil |
| 124 | Cl | H | $CH_3$ | H | |
| 125 | Cl | H | Cl | H | |
| 126 | $OCH_3$ | H | H | H | |

TABLE 6

Het.: $H_1 = $ O⟩N–  
$H_2 = $ O⟩N–

| Compound No. | Het | X | Y | Z | $-NHSO_2CF_3$ | Melting point (°C.) |
|---|---|---|---|---|---|---|
| 127 | $H_1$ | 2-$CH_3$ | | | 3 | 195–200° |
| 128 | $H_2$ | 2-$CH_3$ | | | 3 | 260–264° |
| 129 | $H_1$ | 6-$CH_3$ | | | 3 | 213–216° |
| 130 | $H_2$ | 6-$CH_3$ | | | 3 | 239–244° |
| 131 | $H_1$ | 2-$CH_3$ | 6-$CH_3$ | | 3 | 225–227° |
| 132 | $H_2$ | 2-$CH_3$ | 6-$CH_3$ | | 3 | 275–278° |
| 133 | $H_1$ | 2-$CH_3$ | 4-$CH_3$ | | 3 | 205–207° |
| 134 | $H_2$ | 2-$CH_3$ | 4-$CH_3$ | | 3 | 226–228° |
| 135 | $H_1$ | 4-$CH_3$ | 5-$CH_3$ | | 2 | 134–136° |
| 136 | $H_2$ | 4-$CH_3$ | 5-$CH_3$ | | 2 | |
| 137 | $H_1$ | 4-$CH_2CH_3$ | | | 3 | 160° |
| 138 | $H_2$ | 4-$CH_2CH_3$ | | | 3 | |
| 139 | $H_1$ | 2-$CH_2CH_3$ | 6-$C_2H_5$ | | 3 | 213° |
| 140 | $H_2$ | 2-$CH_2CH_3$ | 6-$C_2H_5$ | | 3 | |
| 141 | $H_1$ | 2-$CH_3$ | 4-$CH_3$ | 6-$CH_3$ | 3 | 235–238° |
| 142 | $H_2$ | 2-$CH_3$ | 4-$CH_3$ | 6-$CH_3$ | 3 | |
| 143 | $H_1$ | 2-$CH_3$ | 6-$C(CH_3)_3$ | | 3 | 245–246° |
| 144 | $H_2$ | 2-$CH_3$ | 6-$C(CH_3)_3$ | | 3 | |
| 145 | $H_1$ | 4-$CH_2CH_3$ | 6-$CH_2CH_3$ | | 3 | 207–208° |
| 146 | $H_2$ | 4-$CH_2CH_3$ | 6-$CH_2CH_3$ | | 3 | |
| 147 | $H_1$ | 4-$C(CH_3)_3$ | | | 3 | |
| 148 | $H_2$ | 4-$C(CH_3)_3$ | | | 3 | |
| 149 | $H_1$ | 4-$CH_3$ | 5-$CH_3$ | | 3 | 171–173° |
| 150 | $H_1$ | 5-$CH_3$ | 6-$CH_3$ | | 2 | 184–187° |
| 151 | $H_1$ | 4-$CH_3$ | | | 2 | 93–96° |
| 152 | $H_1$ | 4-$OCH_3$ | | | 2 | 114–115° |
| 153 | $H_1$ | 4-Cl | 4-Cl | | 2 | 134–135° |
| 154 | $H_1$ | 2-$CH_3$ | 5-$CH(CH_3)_2$ | | 3 | |
| 155 | $H_2$ | 2-$CH_3$ | 5-$CH(CH_3)_2$ | | 3 | |

TABLE 6-continued

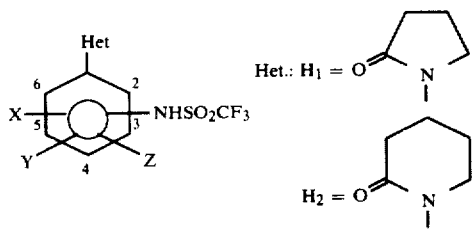

| Compound No. | Het | X | Y | Z | —NHSO$_2$CF$_3$ | Melting point (°C.) |
|---|---|---|---|---|---|---|
| 156 | H$_1$ | 2-CH$_2$CH$_3$ | | | 3 | |
| 157 | H$_2$ | 2-CH$_2$CH$_3$ | | | 3 | |
| 158 | H$_1$ | 4-CH(CH$_3$)$_2$ | | | 3 | |
| 159 | H$_2$ | 4-CH(CH$_3$)$_2$ | | | 3 | |
| 160 | H$_1$ | 4-(CH$_2$)$_3$CH$_3$ | | | 3 | |
| 161 | H$_2$ | 4-(CH$_2$)$_3$CH$_3$ | | | 3 | |
| 162 | H$_1$ | 4-Cl | | | 3 | 157–160° |
| 163 | H$_2$ | 4-Cl | | | 3 | |
| 164 | H$_1$ | 4-Cl | 6-CH$_3$ | | 3 | 219–221° |
| 165 | H$_2$ | 4-Cl | 6-CH$_3$ | | 3 | 247–2508 |
| 166 | H$_1$ | H | | | 3 | 185–187° |
| 167 | H$_2$ | H | | | 3 | 165° |
| 168 | H$_1$ | 4-F | | | 3 | 173–175° |
| 169 | H$_2$ | 4-F | | | 3 | |
| 170 | H$_1$ | 6-OCH$_3$ | | | 3 | 182–184° |
| 171 | H$_2$ | 6-OCH$_3$ | | | 3 | 204–206° |
| 172 | H$_1$ | 4-Cl | 6-Cl | | 3 | 200–201° C. |
| 173 | H$_2$ | 4-Cl | 6-Cl | | 3 | |
| 174 | H$_1$ | 5-Cl | 6-OCH$_3$ | | 3 | |
| 175 | H$_2$ | 5-Cl | 6-OCH$_3$ | | 3 | |
| 176 | H$_1$ | 2-CH$_3$ | 6-Cl | | 3 | |
| 177 | H$_2$ | 2-CH$_3$ | 6-Cl | | 3 | |
| 178 | H$_1$ | 4-OCH$_3$ | | | 3 | 168–169° |
| 179 | H$_2$ | 4-OCH$_3$ | | | 3 | 197° |
| 180 | H$_1$ | 4-OCH$_3$ | 6-OCH$_3$ | | 3 | |
| 181 | H$_2$ | 4-OCH$_3$ | 6-OCH$_3$ | | 3 | |
| 182 | H$_1$ | H | | | 4 | |
| 183 | H$_2$ | H | | | 4 | |
| 184 | H$_1$ | 2-CF | | | 4 | 185–186° |
| 185 | H$_2$ | 2-OCH$_3$ | | | 4 | 195–196° |
| 186 | H$_1$ | 2-OCH$_3$ | | | 4 | 192–194° |
| 187 | H$_2$ | 2-CF$_3$ | | | 4 | |
| 188 | H$_1$ | 3-SO$_2$CH$_3$ | 6-OCH$_3$ | | 4 | |
| 189 | H$_2$ | 3-SO$_2$CH$_3$ | 6-OCH$_3$ | | 4 | |
| 190 | H$_1$ | 3-Cl | 6-OCH$_3$ | | 4 | |
| 191 | H$_2$ | 3-Cl | 6-OCH$_3$ | | 4 | |
| 192 | H$_1$ | 2-Cl | | | 4 | |
| 193 | H$_2$ | 2-Cl | | | 4 | |
| 194 | H$_1$ | 2-CO$_2$CH$_2$CH$_3$ | | | 4 | |
| 195 | H$_2$ | 2-CO$_2$CH$_2$CH$_3$ | | | 4 | |
| 196 | H$_1$ | 3-CO$_2$CH$_2$CH$_3$ | | | 4 | |
| 197 | H$_2$ | 3-CO$_2$CH$_2$CH$_3$ | | | 4 | |
| 198 | H$_1$ | 2-CH$_3$ | 5-Cl | | 4 | |
| 199 | H$_2$ | 2-CH$_3$ | 5-Cl | | 4 | |
| 200 | H$_1$ | H | | | 2 | 84° |
| 201 | H$_2$ | H | | | 2 | |
| 202 | H$_1$ | 4-SO$_2$CH$_2$CH$_3$ | | | 2 | |
| 203 | H$_2$ | 4-SO$_2$CH$_2$CH$_3$ | | | 2 | |
| 204 | H$_1$ | 4-Cl | | | 2 | |
| 205 | H$_2$ | 4-Cl | | | 2 | |
| 206 | H$_1$ | 5-CH$_3$ | 6-Cl | | 2 | |
| 207 | H$_2$ | 5-CH$_3$ | 6-Cl | | 2 | |
| 208 | H$_1$ | 4-O—⟨phenyl-2,4-diCl⟩ | | | 3 | |
| 209 | H$_1$ | 4-O—⟨phenyl-4-CF$_3$⟩ | | | 3 | |
| 210 | H$_2$ | 4-O—⟨phenyl-4-CF$_3$⟩ | | | 3 | |

TABLE 6-continued
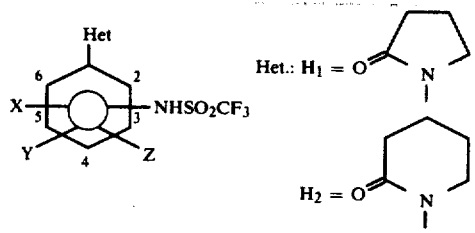
| Compound No. | Het | X | Y | Z | —NHSO₂CF₃ | Melting point (°C.) |
|---|---|---|---|---|---|---|
| 211 | H₁ | 4-CH₂-(3,4-diCl-C₆H₃) | | | 3 | |
| 212 | H₂ | 4-CH₂-(3,4-diCl-C₆H₃) | | | 3 | |
| 213 | H₂ | 4-O-(3,4-diCl-C₆H₃) | | | 3 | |
TABLE 7
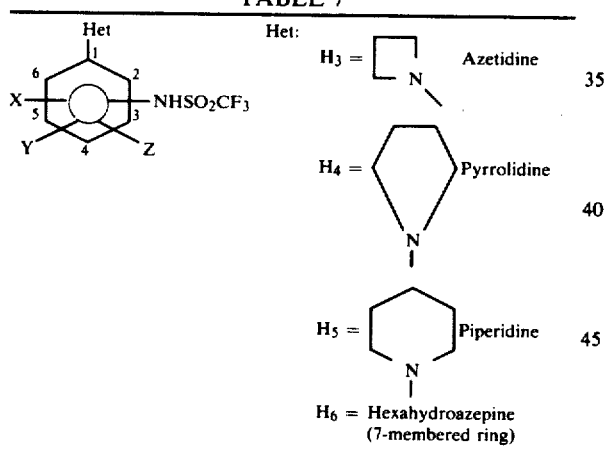
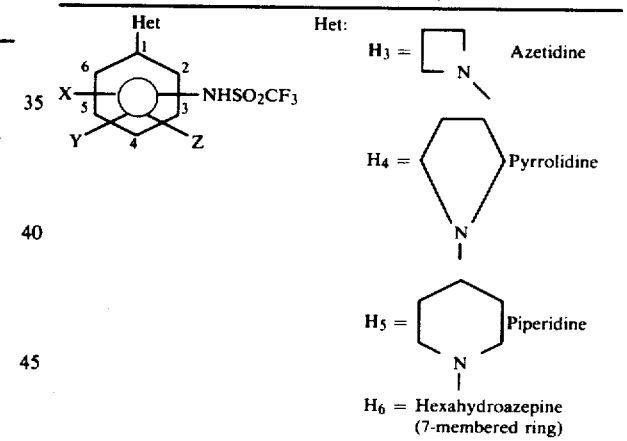
| Compound No. | Het | X | Y | Z | —NHSO₂CF₃ | Melting point (°C.) |
|---|---|---|---|---|---|---|
| 214 | H₃ | 4-CH₃ | | | 3 | |
| 215 | H₃ | 4-CH₃ | 6-CH₃ | | 3 | viscous |
| 216 | H₃ | 4-Cl | | | 3 | |
| 217 | H₃ | 4-Cl | 6-CH₃ | | 3 | |
| 218 | H₄ | 4-CH₃ | | | 3 | 135–139° |
| 219 | H₄ | 4-CH₃ | 6-CH₃ | | 3 | 101–102° |
| 220 | H₄ | 4-Cl | | | 3 | |
| 221 | H₄ | 4-Cl | 6-CH₃ | | 3 | |
| 222 | H₄ | 2-CH₃ | 4-CH₃ | 6-CH₃ | 3 | |
| 223 | H₅ | 4-CH₃ | | | 3 | viscous |
| 224 | H₅ | 4-CH₃ | 6-CH₃ | | 3 | 92–94° |
| 225 | H₅ | 4-Cl | | | 3 | |
| 226 | H₅ | 4-Cl | 6-CH₃ | | 3 | |
| 227 | H₅ | 2-CH₃ | 4-CH₃ | 6-CH₃ | 3 | |
| 228 | H₅ | 4-OCH₃ | | | 3 | |
| 229 | H₆ | 4-CH₃ | | | 3 | 94–98° |
| 230 | H₆ | 4-CH₃ | 6-CH₃ | | 3 | 101–102° |

TABLE 8

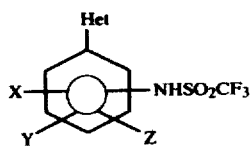

| Compound No. | Het | X | Z | —NHSO$_2$CF$_3$ | Melting point (°C.) |
|---|---|---|---|---|---|
| 231 | 3,4-dimethyl-N-substituted maleimide | 4-CH$_3$ | H | 3 | 152–154° |
| 232 | 3,4-dimethyl-N-substituted maleimide | 4-CH$_3$ | H | 3 | |
| 233 | N-substituted pyrrole | 4-CH$_3$ | H | 3 | |
| 234 | N-substituted pyrrole | 4-CH$_3$ | H | 3 | viscous |
| 235 | 2-(isopropylimino)-N-substituted pyrrolidine | 4-CH$_3$ | H | 3 | |
| 236 | 2-(isopropylimino)-N-substituted pyrrolidine | 4-CH$_3$ | H | 3 | |
| 237 | 2-((4-oxyphenyl)methylimino)-N-substituted pyrrolidine | 4-CH$_3$ | H | 3 | |
| 238 | 2-((4-oxyphenyl)methylimino)-N-substituted pyrrolidine | 4-CH$_3$ | H | 3 | |

TABLE 8-continued

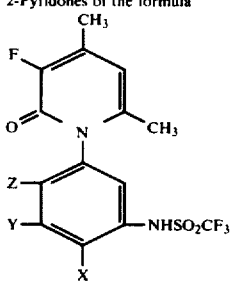

| Compound No. | Het | X | Z | —NHSO$_2$CF$_3$ | Melting point (°C.) |
|---|---|---|---|---|---|
| 239 | (succinimide) | 4-CH$_3$ | H | 3 | 177–179° |

2-Pyridones of the formula

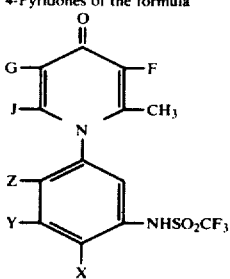

TABLE 9

| Compound No. | X | Y | Z | F | Melting point |
|---|---|---|---|---|---|
| 240 | CH$_3$ | H | H | CN | |
| 241 | CH$_3$ | H | CH$_3$ | CN | 280° |
| 242 | Cl | H | H | CN | 231° |
| 243 | —OCH$_3$ | H | H | CN | 225° |
| 244 | H | H | H | CN | |
| 245 | CH$_3$ | H | H | —COOH | |
| 246 | CH$_3$ | H | CH$_3$ | —COOH | 225° |
| 247 | Cl | H | H | —COOH | |
| 248 | —OCH$_3$ | H | H | —COOH | |
| 249 | H | H | H | —COOH | |
| 250 | CH$_3$ | H | H | —COOCH$_3$ | |
| 251 | CH$_3$ | H | CH$_3$ | —COOCH$_3$ | 196° |
| 252 | Cl | H | H | —COOCH$_3$ | |
| 253 | —OCH$_3$ | H | H | —COOCH$_3$ | |
| 254 | H | H | H | —COOCH$_3$ | |
| 254a | CH$_3$ | H | CH$_3$ | H | 204° |

4-Pyridones of the formula

TABLE 10

| Compound No. | X | Y | Z | F | G | J | Melting point |
|---|---|---|---|---|---|---|---|
| 255 | CH$_3$ | H | H | —COOCH$_3$ | H | CH$_3$ | |
| 256 | CH$_3$ | H | CH$_3$ | —COOCH$_3$ | H | CH$_3$ | 260° (dec.) |
| 257 | Cl | H | H | —COOCH$_3$ | H | CH$_3$ | |
| 258 | —OCH$_3$ | H | H | —COOCH$_3$ | H | CH$_3$ | |
| 259 | H | H | H | —COOCH$_3$ | H | CH$_3$ | |
| 260 | CH$_3$ | H | H | —COOH | H | CH$_3$ | |
| 261 | CH$_3$ | H | CH$_3$ | —COOH | H | CH$_3$ | |
| 262 | Cl | H | H | —COOH | H | CH$_3$ | |
| 263 | —OCH$_3$ | H | H | —COOH | H | CH$_3$ | |
| 264 | H | H | H | —COOH | H | CH$_3$ | |
| 265 | CH$_3$ | H | H | —COOCH$_3$ | Cl | H | |
| 266 | CH$_3$ | H | CH$_3$ | —COOCH$_3$ | Cl | H | 140° (dec.) |
| 267 | Cl | H | CH$_3$ | —COOCH$_3$ | Cl | H | 200° (dec.) |
| 268 | —OCH$_3$ | H | H | —COOCH$_3$ | Cl | H | |
| 269 | H | H | H | —COOCH$_3$ | Cl | H | |

Agents according to the invention are prepared in a manner known per se by intimate mixing and grinding of active ingredients of the formula I with suitable carrier materials, if desired with the addition of dispersing agents or solvents which are inert towards the active ingredients. The active ingredients may exist, and be used, in the following processing forms:

Solid processing forms: dusting agents, sprinkling agents, granules, coated granules, impregnated granules and homogeneous granules;

Active ingredient concentrates which are dispersible in water: wettable powders, pastes and emulsions;

Liquid processing forms: solutions.

In order to prepare solid processing forms (dusting agents, sprinkling agents and granules), the active ingredients are mixed with solid carrier materials. Examples of carrier materials are kaolin, talc, bolus, loess, chalk, limestone, lime grit, attapulgite, dolomite, diatomaceous earth, precipitated silica, alkaline earth metal silicates, sodium and potassium aluminosilicates (feldspars and mica), calcium and magnesium sulphates, magnesium oxide, ground plastics, fertilisers, such as ammonium sulphate, ammonium phosphate, ammonium nitrate and urea, ground vegetable products, such as cereal flour, bark flour, wood flour, nutshell flour, cellulose powder, plant extract residues, active charcoal and the like, in each case on their own or as mixtures with one another.

Granules can be produced by dissolving the active ingredients in an organic solvent and applying the solution thus obtained to a granulated material, for example attapulgite, $SiO_2$, granicalcium or bentonite, and then again evaporating the organic solvent.

Polymer granules can be produced by, for example, impregnating finished, porous polymer granules, such as urea/formaldehyde polymers, polyacrylonitrile and polyesters, having a certain surface area and an advantageous predetermined absorption/desorption ratio, with the active ingredients, for example in the form of their solutions (in a low-boiling solvent) and removing the solvent. Such polymer granules can be applied in the form of micro-granules with bulk densities of, preferably 300 g/liter to 600 g/liter, also with the aid of atomisers. Atomising can be effected over extensive treatment areas with the aid of aircraft.

Granules are also obtainable by compacting the carrier material with the active ingredients and additives and then comminuting the mixture.

Furthermore, it is possible to add to these agents additives which stabilise the active ingredient and/or non-ionic, anionic and cationic substances which, for example, improve the adhesion of the active ingredients to plants and parts of plants (adhesives and glues) and/or ensure better wettability (wetting agents) and dispersibility (dispersing agents). Adhesives are, for example, the following: olein/lime mixture, cellulose derivatives (methylcellulose and carboxymethylcellulose, hydroxyethylene glycol ethers of mono- and di-alkylphenols having 5 to 15 ethylene oxide residues per molecule and 8 to 9 carbon atoms in the alkyl radical, ligninsulphonic acid, its alkali metal salts and alkaline earth metal salts, polyethylene glycol ethers (Carbowaxes), fatty alcohol polyglycol ethers having 5 to 20 ethylene oxide radicals per molecule and 8 to 18 carbon atoms in the fatty alcohol moiety, condensation products of ethylene oxide and propylene oxide, polyvinylpyrrolidones, polyvinyl alcohols, condensation products of urea/formaldehyde and latex products.

Water-dispersible active ingredient concentrates, i.e. wettable powders, pastes and emulsion concentrates, are agents which can be diluted with water to any desired concentration. They consist of active ingredient, carrier material and, if appropriate, additives which stabilise the active ingredient, surfactants and anti-foams and, if desired, solvents.

The wettable powders and pastes are obtained by mixing and grinding the active ingredients with dispersing agents and pulverulent carrier materials in suitable devices until homogeneity is achieved. Carrier materials are, for example, those mentioned above for the solid processing forms. In some cases it is advantageous to use mixtures of different carrier materials. Dispersing agents which can be used are, for example: condensation products of sulphonated naphthalene and sulphonated naphthalene derivatives with formaldehyde, condensation products of naphthalene or of naphthalenesulphonic acids with phenol and formaldehyde, and alkali metal salts, ammonium salts and alkaline earth metal salts of ligninsulphonic acid, as well as alkylarylsulphonates, alkali metal salts and alkaline earth metal salts of dibutylnaphthalenesulphonic acid, fatty alcohol-sulphates, such as salts of sulphated hexadecanols and heptadecanols and salts of sulphated fatty alcohol polyethylene glycol ether, the sodium salt of oleyl methyl tauride, di-tertiary ethylene glycols, dialkyldilaurylammonium chloride and fatty acid salts of alkali metals and alkaline earth metals.

Anti-foams are, for example, silicones.

The active ingredients are mixed, ground, sieved and strained with the abovementioned additives in such a way that the particle size of the solid component does not exceed 0.02 to 0.04 mm in the case of wettable powders and 0.03 mm in the case of pastes. To prepare emulsion concentrates and pastes, dispersing agents, such as have been listed in the preceding sections, organic solvents and water are used. Solvents are, for example: alcohols, benzene, xylenes, toluene, dimethylsulphoxide, N,N-dialkylated amides and trialkylamines. The solvents must be virtually odourless, not phytotoxic and inert towards the active ingredients and must not be readily combustible.

Furthermore, the agents according to the invention can be used in the form of solutions. For this purpose, the active ingredient, or several active ingredients, of the formula I is or are dissolved in suitable organic solvents, solvent mixtures, water or mixtures of organic solvents and water. Organic solvents which can be used are aliphatic and aromatic hydrocarbons, their chlorinated derivatives and alkylnaphthalenes, on their own or as mixtures with one another.

The content of active compound in the agents described above is between 0.1 and 95%, preferably between 1 and 80%. Use forms can be diluted down to 0.001%. The amounts applied are as a rule 0.1 to 10 kg of active substance/hectare and preferably 0.25 to 5 kg of active substance/hectare. The active compounds of the formula I can be formulated, for example, as follows (parts are by weight):

Dusting agents

The following substances are used to prepare (a) a 5% strength dusting agent and (b) a 2% strength dusting agent:

(a)
5 parts of 1-(3'-trifluoromethanesulphonamido-4'-chloro-6'-methylphenyl)-pyrrolidin-2-one and
95 parts of talc;

(b)
2 parts of 1-(3'-trifluoromethanesulphonamido-4',6'-dimethylphenyl)-3-carboxy-4,6-dimethyl-2-pyridone,
1 part of highly disperse silica and
97 parts of talc;

The active ingredients are mixed and ground with the carrier substances.

Granules

The following substances are used to prepare 5% strength granules:

5 parts of 1-(3'-trifluoromethanesulphonamido-4',6'-dimethylphenyl)-3-methoxycarbonyl-4,6-dimethyl-2-pyridone,
0.25 part of epoxidised vegetable oil,
0.25 part of cetyl polyethylene glycol ether with 8 mols of ethylene oxide,
3.50 parts of polyethylene glycol and
91 parts of kaolin (grain size 0.3 to 0.8 mm).

The active substance is mixed with epoxidised vegetable oil and the mixture is dissolved in 6 parts of acetone, and polyethylene glycol and cetyl polyethylene glycol ether are then added. The solution thus obtained is sprayed onto kaolin and the acetone is then evaporated in vacuo.

Wettable powders

The following constituents are used to prepare (a) a 50% strength wettable powder, (b) a 25% strength wettable powder and (c) a 10% strength wettable powder:

(a)
50 parts of 1-(3'-trifluoromethanesulphonamido-4',6'-dimethylphenyl)-3-cyano-4,6-dimethyl-2-pyridone,
5 parts of sodium dibutylnaphthylsulphonate,
3 parts of a 3:2:1 naphthalenesulphonic acids/phenolsulphonic acids/formaldehyde condensation product,
20 parts of kaolin and
22 parts of Champagne chalk;

(b)
25 parts of the diethanolamine salt of the above active ingredient,
5 parts of the sodium salt of oleyl methyl tauride,
2.5 parts of a naphthalenesulphonic acids/formaldehyde condensation product,
0.5 part of carboxymethylcellulose,
5 parts of neutral potassium aluminosilicate and
62 parts of kaolin;

(c)
10 parts of the active ingredient according to Example 3,
3 parts of a mixture of the sodium salts of saturated fatty alcohol sulphates,
5 parts of a naphthalenesulphonic acids/formaldehyde condensation product and
82 parts of kaolin.

The indicated active ingredient is applied to the corresponding carrier materials (kaolin and chalk) and these are then mixed and ground. This gives wettable powders of outstanding wettability and outstanding suspension properties. Suspensions having any desired concentration of active ingredient can be obtained from such wettable powders by dilution with water. Such suspensions are used for combating weeds and wild grasses in cultivated plants by the preemergence process and for treating lawns.

Paste

The following substances are used to prepare a 45% strength paste:

45 parts of 1-(3'-trifluoromethanesulphonamido-4',6'-dimethylphenyl)-5-methylpyrrolidin-2-one,
5 parts of sodium aluminosilicate,
14 parts of cetyl polyethylene glycol ether with 8 mols of ethylene oxide,
1 part of oleyl polyethylene glycol ether with 5 mols of ethylene oxide,
2 parts of spindle oil,
23 parts of water and
10 parts of polyethylene glycol.

The active ingredient is intimately mixed and ground with the additives in equipment suitable for this purpose. This gives a paste, from which suspensions of any desired concentration can be prepared by dilution with water. The suspensions are suitable for treating lawns.

Emulsifiable concentrate

In order to prepare a 25% strength emulsifiable concentrate 25 parts of 1-(3'-trifluoromethanesulphonamido-4',6'-dimethylphenyl)-pyrrolidin-2-one,
5 parts of a mixture of polyoxyethyleneated nonylphenol and calcium dodecylbenzene-sulphonate,
35 parts of 3,5,5-trimethyl-2-cyclohexen-1-one and
35 parts of dimethylformamide
are mixed together. This concentrate can be diluted with water to give emulsions of suitable concentrations.

In place of the particular active ingredient indicated in the above formulation examples, it is also possible to use another compound which falls under the formula I.

Aqueous concentrate

In order to prepare a 25% strength aqueous concentrate
25 parts of 1-(3'-trifluoromethanesulphonamido-4',6'-dimethylphenyl)-pyrrolidin-2-one,
8 parts of di-(2-hydroxyethyl)-amine,
1 part of octylphenol polyglycol ether and
66 parts of water
are mixed together. This concentrate can be diluted to a suitable concentration with water.

The active ingredients contained in the agents according to the invention regulate plant growth in various ways. Thus, in particular, they inhibit, retard or prevent growth and germination. Accordingly, these agents both have a pre-emergence and post-emergence herbicidal action and also inhibit growth.

Agents, according to the invention, which contain at least one compound of the formula I as the active component are especially suitable for inhibiting and regulating plant growth in monocotyledonous and dicotyledonous plants, such as grasses, shrubs, trees, cereal crops and crops of leguminosae, sugar cane, tobacco, soya, onion and potato tubers, ornamental plants, fruit trees and vines.

The effect achieved in particular by the novel active compounds of the formula I is the desired reduction in the size of the plants, especially in the height of growth. In general, this is associated with a certain change in the shape of the plant. The plant is strengthened in direct relationship to the reduction in the height of growth. Leaves and stems are more robust. By shortening the internodal distances in monocotyledonous plants, the buckling resistance is increased. In this way, crop losses due to thunderstorms, continual rain and the like, which normally result in lodging of crops of cereals and leguminosae, can be largely prevented, and harvesting can thus be facilitated. As a side effect, the reduced height of growth in crop plants results in a saving of fertilisers. This also applies equally to ornamental plants, ornamental lawns, sports fields or other open spaces.

One of the most important problems in areas in which grass only is cultivated is, however, grass cutting itself, whether in open spaces in urban areas, on industrial sites, on sports pitches, alongside motorways or on airfields, railway embankments or the sloping banks of waterways. In all these cases it is necessary to mow the turf or the growth of grass periodically. This is not only very expensive in terms of labour and machinery but, in the transport sector, also involves considerable dangers for the personnel concerned and for road users.

There is, therefore, particularly in areas with large traffic networks, an urgent need on the one hand to maintain and care for the greensward which is necessary to strengthen road shoulders and embankments on traffic routes and, on the other hand, to keep it at a medium height of growth during the whole vegetation period, using simple methods. This need is met in a very advantageous manner by applying active compounds, according to the invention, of the formula I.

In an analogous manner, the labour-intensive pruning work can be reduced by treating trees, shrubs and hedges, especially in urban and industrial areas, with compounds, according to the invention, of the formula I.

The shoot growth and/or the fertility of fruit trees and vines can also be influenced in an advantageous manner by the use of active compounds, according to the invention, of the formula I.

Ornamental plants with a vigorous growth in height can be cultivated as compact pot plants by treatment with active compounds according to the invention.

The active compounds of the formula I are also used for inhibiting the growth of undesired side shoots, for example in tobacco and ornamental plants, which eliminates the labour-intensive breaking off of the shoots by hand, and also for inhibiting sprouting of stored tubers, for example ornamental plant tubers, onions and potatoes, and finally for increasing the yield of cultivated plants with a pronounced vegetative growth, such as soya and sugar cane, by accelerating the transition from the vegetative to the generative growth phase by application of active compounds according to the invention.

The active compounds, according to the invention, of the formula I are preferably employed for inhibiting the growth of grasses, cereal crops, tobacco, soya and ornamental plants.

The amounts applied vary and depend on the time of application. In general they are between 0.1 and 5 kg of active compound per hectare when applied before emergence of the plants and preferably up to 4 kg per hectare for the treatment of standing crops.

The action of the active compounds according to the invention takes place both via the parts of plants above the soil (contact action), especially the leaves, and via the soil, as a pre-emergence herbicide (inhibition of germination).

The action of the compounds as powerful growth inhibitors manifests itself by the fact that most species of plants treated after-emergence display cessation of growth after a test period of three weeks, the treated parts of the plants assuming a dark green coloration. However, the leaves do not drop off.

In some species of plants, growth is already inhibited with a dosage of 0.5 kg/hectare and below.

Since not all species of plants are inhibited to the same extent, selective use of the compounds is possible by choosing a specific low dosage.

Many of the active compounds according to the invention are also highly active herbicides against many weeds, both against monocotyledonous weeds and dicotyledonous weeds, when applied before-emergence, even in relatively low concentrations. In medium concentrations, they also have a strong herbicidal action when applied after-emergence. Many active compounds tend to a total herbicidal action and others, for example compound No. 84, are suitable for use as good selective herbicides, especially in crops of sugar beet.

In areas where there is an increased danger of erosion, the active compounds according to the invention can be employed as growth inhibitors in very diverse crops.

In this case the weed cover is not eliminated but merely so greatly inhibited that competition with the cultivated plants no longer arises.

The novel active compounds of the formula I are distinguished, moreover, by a very powerful pre-emergence herbicidal action and are thus also pronounced germination inhibitors.

The following test methods were used to demonstrate the usefulness of the compounds as herbicides (pre-emergence and post-emergence) and as growth inhibitors:

Pre-emergence herbicidal action (inhibition of germination)

Immediately after sowing the test plants in seed trays, in a greenhouse, the surface of the soil is treated with an aqueous suspension of the active compounds, obtained from a 25% strength wettable powder. Different concentration series were used, ranging from 0.05 to 4 kg of active substance per hectare. The seed trays are kept in the greenhouse at 22°–25° C. and 50–70% relative atmospheric humidity and the test was evaluated after 3 weeks and the results rated in accordance with the following linear scale:

1 = plants have not germinated or have completely died off

2–8 = intermediate stages of damage

9 = plants undamaged (like untreated control plants).

The test plants used were:

| | |
|---|---|
| hordeum (barley) | setaria italica |
| triticum (wheat) | enchinochloa crus galli |
| zea (maize) | beta vulgaris |
| sorghum hybr. (millet) | sida spinosa |
| oryza (rice) | sesbania exaltata |
| glycine (soya) | amaranthus retroflexus |
| gossypium (cotton) | sinapis alba |
| avena fatua | ipomoea purpurea |
| lolium perenne | galium aparine |
| alopecurus myosuroides | pastinaca sativa |
| bromus tectorum | rumex sp. |
| cyperus esculentus | chrysanthemum leucum. |
| rottboellia exaltata | abutilon sp. |
| digitaria sanguinalis | solanum nigrum |

The active compounds of Examples 2 and 4 resulted in virtually complete inhibition of germination in very many test plants even when applied in a dosage of 0.1 kg/hectare and are clearly superior to the active compounds of U.S. Pat. No. 3,920,444 and German Offenlegungsschrift No. 2,364,144.

Post-emergence herbicidal action (contact herbicide)

A relatively large number (at least 7) of weeds and cultivated plants, both monocotyledonous and dicotyledonous, were sprayed after emergence (in the 4-leaf to 6-leaf stage) with an aqueous emulsion of the active ingredient in dosages of 0.05 to 4 kg of active substance per hectare, spraying being onto the plants, and the plants were kept at 24°–26° C. and 45–60% relative atmospheric humidity. The test was evaluated 5 days and 15 days after the treatment and the result was rated as in the pre-emergence test, in accordance with the same linear scale.

The compounds according to the present invention which were tested displayed a pronounced contact herbicidal action on some plants, and on many plants cessation of growth as a symptom of the growth-inhibiting properties.

Inhibition of the growth of grasses

Seeds of the grasses *Lolium perenne, Poa pratensis, Festuca ovina* and *Dactylis glomerata* were sown in plastic trays containing an earth/peat/sand mixture (6:3:1) and watered normally. After emergence, the grasses were cut back weekly to a height of 4 cm and 40 days after sowing and 1 day after the last cutting were sprayed with aqueous spray liquors of an active compound of the formula I. The amount of active compound, calculated per hectare, was 0.5 to 5 kg of active substance. The growth of the grasses was assessed 10 and 21 days after application.

Inhibition of the growth of cereals

Summar wheat (*Triticum aestivum*), summer barley (*Hordeum vulgare*) and rye (Secale) were sown in sterilised soil in plastic beakers and grown in a greenhouse. 5 days after sowing, the cereal shoots were treated with a spray liquor of the active compound. The leaf application corresponded to 0.1 to 5 kg of active compound per hectare. The evaluation was made after 21 days.

The active compounds according to the invention effect a noticeable inhibition of growth both in grasses and in cereals.

If the main patent is granted, the claims accompanying this application for a patent of addition are intended to extend only to those parts of the invention which are not already covered by the claims of the main patent.

What is claimed is:

1. A compound of the formulae Ia or Ib.

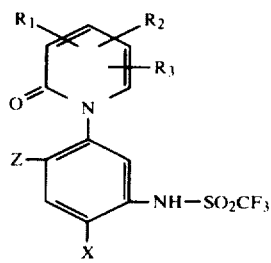

(Ia)

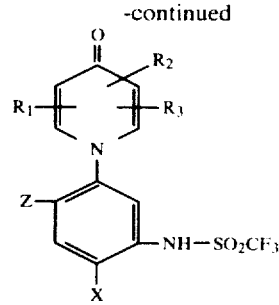

(Ib)

or a salt thereof formed with a cation selected from the group consisting of alkali metals, alkaline earth metals, zinc, copper, iron and organic amines, in which formulae $R_1$, $R_2$ and $R_3$ independently of one another are hydrogen, $C_1-C_4$ alkyl, $C_1-C_4$ alkoxy, alkoxycarbonyl having 1 to 4 carbon atoms in the alkyl portion, carboxyl, halogen or cyano, and X and Z independently of one another are hydrogen, $C_1-C_4$ alkyl, $C_1-C_5$ alkoxy or halogen.

2. A compound according to claim 1, wherein the heterocyclic ring can be substituted by carboxyl, alkoxycarbonyl and one or more radicals selected from the group halogen, cyano or alkyl.

3. The compound 1-(3'-trifluoromethanesulfonamido-4',6'-dimethylphenyl)-3-cyano-4,6-dimethyl-2-pyridone.

4. The compound 1-(3'-trifluoromethanesulfonamido-4',6'-dimethylphenyl)-3-carboxyl-4,6-dimethyl-2-pyridone.

5. The compound 1-(3'-trifluoromethanesulfonamido-4',6'-dimethylphenyl)-3-methoxycarbonyl-4,6-dimethyl-2-pyridone.

6. A composition for regulating plant growth which contains, in addition to carrier materials, an effective plant growth regulating amount of at least one trifluoromethanesulphonamido-phenyl-substituted heterocyclic compound according to claim 1 as the active component.

7. A process for inhibiting and suppressing the plant growth of monocotyledonous and dicotyledonous plants, which comprises the pre-emergence or post-emergence treatment of the sown areas or of the plants with an effective growth inhibiting amount of an active compound according to claim 1.

8. A process for inhibiting the growth of grasses, cereal crops, tobacco, soya and ornamental plants, which comprises the post-emergence treatment of these plants with an effective growth inhibiting amount of an active compound according to claims 1.

* * * * *